(12) United States Patent
O'Brien et al.

(10) Patent No.: US 6,420,408 B1
(45) Date of Patent: Jul. 16, 2002

(54) TRICYCLIC SULFONAMIDES AND THEIR DERIVATIVES AS INHIBITORS OF MATRIX METALLOPROTEINASES

(75) Inventors: Patrick Michael O'Brien, Stockbridge; Joseph Armand Picard, Canton; Drago Robert Sliskovic, Saline, all of MI (US)

(73) Assignee: Warner-Lambert Company, Morris Plains, NJ (US)

( * ) Notice: Subject to any disclaimer, the term of this patent is extended or adjusted under 35 U.S.C. 154(b) by 0 days.

(21) Appl. No.: 09/719,027

(22) Filed: Apr. 10, 2001

Related U.S. Application Data

(60) Provisional application No. 60/095,006, filed on Jul. 30, 1998.

(51) Int. Cl.$^7$ ................ A61K 31/4178; A61K 31/404; A61K 31/343; C07D 405/12; C07D 307/91
(52) U.S. Cl. .............. 514/389; 514/392; 514/414; 514/468; 549/458; 549/461; 548/311.4; 548/454
(58) Field of Search ................ 549/458, 461; 548/311.4, 454; 514/389, 392, 414, 468

(56) References Cited

U.S. PATENT DOCUMENTS 3,784,602 A * 1/1974 Frei et al. .................... 544/145

FOREIGN PATENT DOCUMENTS

| DE | 2 033 959 | 2/1971 |
| EP | 0 555 824 A1 | 8/1993 |
| WO | WO 96/38434 | 12/1996 |
| WO | WO 98/06711 | 2/1998 |
| WO | WO 98/09934 | 3/1998 |
| WO | WO 98/09957 | 3/1998 |
| WO | WO 98/16503 | 4/1998 |

OTHER PUBLICATIONS

Aisen P.S., "Anti–inflammatory therapy for Alzheimer's disease", *Neurobiology of Aging*, vol. 21, pp. 447–448 (2000).

Andersen, K. et al., "Do nonsteroidal anti–inflammatory drugs decrease the risk for Alzheimer's disease? The Rotterdam Study", *Neurology*, vol. 45, pp. 1441–1445 (Aug. 1995).

Andrews, H.J. et al., "A synthetic peptide metalloproteinase inhibitor, but not Timp, prevents the breakdown of proteoglycan within articular cartilage in vitro", *Agents Actions*, vol. 37, pp. 147–154 (1992).

Armstrong, P.W. et al., "Structural remodeling in heart failure: gelatinase induction", *Can. J. Cardiol.*, vol. 10, No. 2, pp. 214–220 (Mar. 1994).

Bagchus, W.M. et al., "Glomerulonephritis Induced by Monoclonal Anti–Thy 1.1 Antibodies: A Sequential Histological and Ultrastructural Study in the Rate", *Laboratory Investigation*, vol. 55, No. 6, pp. 680–687 (1986).

Bendeck, M.P. et al., "Smooth muscle cell migration and matrix metalloproteinase expression after Arterial injury in the rat", *Circulation Research*, vol. 75, No. 3, pp. 539–545 (Sep. 1994).

Benelli, R. et al., "Inhibition of AIDS–Kaposi's Sarcoma Cell Induced Endothelial Cell Invasion by TIMP–2 and a Synthetic Peptide from the Metalloproteinase Propeptide: Implications for an Anti–Angiogenic Therapy", *Oncology Research*, vol. 6, No. 6, pp. 251–257 (1994).

Breitner, J.C.S. et al., "Inverse association of anti–inflammatory trreatments and Alzheimer's disease: Initial results of a co–twin control study", *Neurology*, 44: 227–232 (Feb. 1994).

Breitner, J.C.S. et al., "Delayed onset of Alzheimer's disease with nonsteroidal anti–inflammatory and histamine H2 blocking drugs", *Neurobiol. Aging*, vol. 16, No. 4, pp. 523–530 (1995).

Brown, P. et al., "Independent Expression and Cellular Processing of $M_r$ 72,000 Type IV Collagenase and Interstitial Collagenase in Human Tumorigenic Cell Lines", *Cancer Research*, vol 50, pp. 6184–6191 (Oct. 1, 1990).

Brown, S.I. et al., "Collagenolytic activity of alkali burned corneas", *Arch. Ophtalmol.*, vol. 81, pp. 370–373 (Mar. 1969).

Burns, F. et al., *Invest. Ophtalmol.*, vol. 30, No. 7, pp. 1569–1575 (Jul. 1989).

Cagniant, P. et al., "Etude de la succinoylation et de la glutaroylation du tetrahydro1,2,3,4 dibenzofurannne; nouvelle sythesis du β–brazane" *bulletin De La Societe Chimique De France*, No. 12, pp. 4435–442 (1971).

"The Canadian Study of Helath and Aging: Risk factors for Alzheimer's disease in Canada", *Neurology*, vol. 44, pp. 2073–2080 (Nov. 1994).

Clark, R.K. et al., "Development of tissue damage, inflammation and resolution following stroke: an immunohistochemical and quantitative planimetric study", *Brain Research Bulletin*, vol. 31, pp. 565–572 (1993).

(List continued on next page.)

*Primary Examiner*—Laura L. Stockton
(74) *Attorney, Agent, or Firm*—Merchant & Gould P.C.

(57) ABSTRACT

Tricyclic sulfonamide compounds and derivatives are described as well as methods for the preparation and pharmaceutical compositions of same, which are useful as inhibitors of matrix metalloproteinases, particularly gelatinase A, collagenase-3, and stromelysin-1 and for the treatment of multiple sclerosis, atherosclerotic plaque rupture, aortic aneurysm, heart failure, left ventricular dilation, restenosis, periodontal disease, or other autoimmune or inflammatory disorders dependent upon tissue invasion by leukocytes or other activated migrating cells, acute and chronic neurodegenerative disorders including stroke, head trauma, spinal cord injury, Alzheimer's disease, amyotrophic lateral sclerosis, cerebral amyloid angiopathy, AIDS, Parkinson's disease, Huntington's disease, prion diseases, myasthenia gravis, and Duchenne's muscular dystrophy.

31 Claims, No Drawings

OTHER PUBLICATIONS

Davies, B. et al., "A synthetic Matrix Metalloproteinase Inhibitor Decreases Tumor Burden and Prolongs Survival of Mice Bearing Human Ovarian Carcinoma Xenografts", *Cancer Reasearch*, vol. 53, pp. 2087–2091 (May 1, 1993).

Davies, M. et al., "Proteinases and glomerular matrix turnover", *Kidney International*, vol. 41, pp. 671–678 (1992).

DeClerck, Y. et al., "Inhibition of Invasion and Metastasis in Cells Transfected with an Inhibitor of Metalloproteinases", *Cancer Res.*, vol. 52, pp. 701–708 (Feb. 1, 1992).

Ellis, A.J. et al, "The Prevention of Collagen Breakdown in Bovine Nasal Cartilage by TIMP, TIMP-2 and a Low Molecular Weight Synthetic Inhibitor", *Biochemical and Biophysical Research Communications*, vol. 201, No. 1, pp. 94 101 (May 30, 1994).

Freije, Jos´´ et al. *Journal of BiologicalChemistry*, vol. 269, No. 24, pp. 16766–16773 (1994).

Galis, Z. et al, "Increased expression of matrix metalloproteinases and matrix degrading activity in vulnerable regions of human atherosclerotic plaques", *J. Clinical Invest.*, vol. 94, pp. 2493–2503 (Dec. 1994).

Gendelman, H. et al., "Macrophages/microglia and the pathoophysiology of CNS injuries in AIDS", *Journal of Leukocyte Biology*, vol. 56, pp. 387–388 (Sep. 1994).

Gijbels, K. et al., *J. Clin. Invest.*, vol. 94, pp. 2177–2182 (Dec. 1994).

Giulian D. et al., "Infammatory glia mediate delayed neuronal damage after ischemia in the central nervous system", *Inflammatory Neurotoxins and Stroke/Supplement I Stroke*, vol. 24, No. 12, pp. 184–190 (Dec. 1993).

Grams, F. et al., "X–ray structures of human neutrophil collagenase complexed with peptide hydroxamate and peptide thiol inhibitors: Implications for substrate binding and rational drug design", *Eur. J. Biochem*, vol. 228, pp. 830–841 (1995).

Hampel, H. et al, "Inflammatory and Immunological Mechanisms in Alzheimer's Disease", *DN&P*, vol. 8, No. 10, pp. 599–608 (Dec. 1995).

Henney A. et al., "Localization of stromelysin gene expression in atherosclerotic plaques in situ hybridization", *Proc. Nat'l. Acad. Sci.*, vol. 88, pp. 8154–8158 (Sep. 1991).

Keumi, T. et al. *Chemical Abstracts*, vol. 88, No. 21, Abstract No. 152329u, p. 581, 1978.

Kitamura, M. et al. "Gene transfer of metalloproteinase transin induces aberrant behavior of cultured mesangial cells", *Internatioal Society of Nephrology*, vol. 45, pp. 580–1586 (1994).

Lee, T. et al., "Impact of Left Ventricular Size on the Surival in Advanced Heart Failure", *Am. J. Cardiol.*, vol. 72, pp. 672–676 (Sep. 5, 1993).

Leigh P.N., "Pathogenic Mechanisms in Amyotiphic Lateral Sclerosis and Other Motor Neuron Disorders", *Neurodegenerative Diseases*, W.B. Sanders Company, Chapter 28, pp. 473–488 (1994).

Lovett, D. et al., "Structural Characterization of the Mesangial Cell Type IV Collagenase and Enhanced Expression in a Model of Immune Complex–mediated Glomerulonephritis", *American J. of Pathology*, vol. 141, No. 1, pp. 85–98 (Jul. 1992).

Lucca, U. et al., "Nonsteroidal Antiinflammatory Drug Use in Alzheimer's Disease", *Society of Biological psychiatry*, vol. 36, pp. 854–866 (1994).

Mandybur T.I., et al. "Cerebral Amyoid Angiopathy With Granulomatous Ameliorated by Steroidi–Cytoxan Treatment", *Clin. Neuropharm.*, vol. 15, No. 3, pp. 241–247 (1992).

Marti, H. et al., "Homology cloning of rat 72 kDa type IV collagenase: cytokine and second–messenger inducibility in glomerular mesangial cells", *Biochem. J.*, vol. 291, pp. 441–446 (1993).

Marti, H.P. et al., "Transforming Growth Factor–β1 Stimulates Glomerular Mesangial Cell Synthesis of the 72–kd Type IV Collagense", *American Journal of Pathology*, vol. 144, No. 1, pp. 82–94 (Jan. 1994).

Martin, J., et al., "Enhancement of Glomerular Mesangial Cell Neutral Proteinase Secretion by Macrophages: role of Interleukin", *Journal of Immunology*, vol. 137, No. 2, pp. 525–529 (Jul. 15, 1986).

Martin R. et al., "Immunological Aspects of Demyelinating Diseases", *Annul Rev. Immunol.* vol. 10, pp. 153–187 (1992).

Martin, R. et al., "Immunological Aspects of Experimental Allergic Encephalomyelitis and Multiple Sclerosis", *Critical Review in Clinical Laboratory Sciences*, vol. 32, No. 2, pp. 121–182 (1995).

McGeer, E., "Neurodegeneration and the Immune System", In: *Neurodegenative Diseasaes*, W.B. Saunders, Chapter 18, pp. 277–300 (1994).

McGeer, P. et al., "Anti–inflammmatory agents as a therapeutic approach to Alzheimer's disease", *Neurology*, vol. 42, pp. 447–449 (Feb., 1992).

McGeer, P. et al., Neuroimmune Mechanisms in Alzheimer Disease Pathogenesis, *Alzheimer Disease and Associated Disorders*, vol. 8, No. 3, pp. 149–158 (1994).

Melchiori, A. et al., "Inhibition of Tumor Cell Invasion by a Highly Conserved Peptide Sequence from the Matrix Metalloproteinase Enzyme Prosegment", *Cancer Res.*, vol. 52, pp. 2353–2356 (Apr. 15, 1992).

Monsky, W. et al., "Binding and Localization of $M_2$ 72,000 Matrix Metalloproteinase at Cell Surface Invadopodia", *Cancer Research*, vol. 53, pp. 3159–3164 (1993).

Overall, C.M. et al., "Demonstrations of tissue collagenase activity in vivo and its relationship to inflammation severity in human gingiva", *Journal of Periodontal Research*, vol. 22, pp. 81–88 (1987).

Patterson, P., "Cytokines in Alzheimer's disease and multiple sclerosis", *Current Opinion in Neurobiology*, vol. 5, pp. 642–646 (1995).

Pauly, R. et al., "Migration of Cultured Vascular Smooth Muscle Cells Through a Basement Membrane Barrier Requires Type IV Collagenase Activity and Is Inhibited by Cellular Differentiation", *Circulation Research*, vol. 75, No. 1, pp. 41–54 (Jul. 1994).

Reddy, H.K. et al., 'Abstract' "Activated myocardial collagenase in idiopathic dilated cardiomyopathy: A marker of dilation and remodeling", *Clinical Research*, vol. 41, No. 3, p. 660A (1993).

Rich, J.B. et al., "Nonsteroidal anti–inflammatory drugs in Alzheimer's disease", *Neurology*, vol. 45, pp. 51–55 (1995).

Rogers, J. et al., "Inflammation and Alzheimer's Disease Pathogenesis", *Neurobiology of Aging*, vol. 17, No. 5, pp. 681–686 (1996).

Romanic, A. et al., "The Induction of 72–kDa Gelatinase in T Cells upon Adhesion to Endothelial Cells is VCAM–1 Dependent", *The Journal of Cell Biology*, vol. 125, pp. 1165–1178 (Jun. 1994).

Rotherwell, N.J. et al., "Involvement of Cytokines in Acute Neurodegeneration in the CNS", *Neuroscience and Biobehavioral Reviews*, vol. 17, pp. 217–227 (1993).

Saarialho–Kere, U. et al., "Distinct Populations of Basal Keratinocytes Express Stromelysin–1 and Stromelysin–2 in Chronic Wounds", *J. Clin. Invest.*, vol. 94, pp. 79–88 (Jul. 1994).

Sabbah, H. et al, "Left ventricular shape changes during the course of evolving heart failure", *The American Physiological Society*, vol. 263, pp. H266–H270 (1992).

Sato, H. et al, "A matrix metalloproteinase expressed on the surface of invasive tumor cells", *Nature*, vol. 370, pp. 61–65 (Jul. 7, 1994).

Strongin, A. et al., "Plasma Membrane–dependent Activation of the 72–kDa Type IV Collagenase Is Prevented by Complex Formation with TIMP–2", *The Journal of Biological Chemistry*, vol. 268, No. 19, pp. 14033–14039 (Jul. 5, 1993).

Taraboletti, G. et al., "Inhibition of Angiogenesis and Murine Hemangioma Growth by Batimastat, a Synthetic Inhibitor of Matrix Metalloproteinases", *Journal of the National Cancer Institue*, vol. 87, No. 4, pp. 293–298 (Feb. 15, 1995).

Turck, J. et al., "Matrix Metalloproteinase 2 (Gelatinase A) Regulaes Glomerular Mesangial Cell Proliferation and Differentiation", *The Journal of Biological Chemistry*, vol. 271, No. 25, pp. 15074–15083 (Jun. 21, 1996).

Uitto, V.J. et al., "Collagenase and neutral metalloproteinase activity in extracts from inflamed human gingival", *Journal of Periodontal Research*, vol. 16, pp. 417–424 (1981).

Vincenti, M. et al., "Using Inhibitors of Metalloproteinases to Treat Arthritis", *Athritis & Rheumatism*, vol. 37, No. 8, pp. 1115–1126 (Aug. 1994).

Vine, N. et al., "Metalloproteinases in degenerative aortic diseases", *Clinical Science*, vol. 81, pp. 233–239 (1991).

Walakovits, L. et al., "Detection of Stromelysin and Collagenase in Synovial Fluid from Patients with Rheumatoid Arthritis and Posttraumatic Knee Injury", *Arthritis and Rheumatism*, vol. 35, No. 1, pp. 35–42 (Jan. 1992).

Woessner Jr., J. "Matrixi metalloproteinases and their inhibitors in connective tissue remodeling", *The FASEB Journal*, vol. 5, pp. 2145–2154 (May 1991).

Zafarullah, M. et al., "Elevated Metalloproteinases and Tissue Inhibitor of Metalloproteinase mRNA in Human Osteoarthritic Synovia", *The Journal of Rheumatology*, vol. 20, No. 4, pp. 693–697 (1993).

* cited by examiner

TRICYCLIC SULFONAMIDES AND THEIR DERIVATIVES AS INHIBITORS OF MATRIX METALLOPROTEINASES

This application is a 371 of PCT/US99/12273 filed Jun. 2, 1999 which claims the benefit of U.S. Provisional No. 60/095,006 filed Jul. 30, 1998.

BACKGROUND OF THE INVENTION

The present invention relates to novel tricyclic sulfonamide compounds and their derivatives useful as pharmaceutical agents, to methods for their production, to pharmaceutical compositions which include these compounds and a pharmaceutically acceptable carrier, and to pharmaceutical methods of treatment. The novel compounds of the present invention are inhibitors of matrix metalloproteinases, e.g., gelatinase A (MMP-2), collagenase-3 (MMP-13), and stromelysin-1 (MMP-3). More particularly, the novel compounds of the present invention are useful in the treatment of atherosclerotic plaque rupture, aortic aneurism, heart failure, left ventricular dilation, restenosis, periodontal disease, corneal ulceration, treatment of burns, decubital ulcers, wound repair, cancer, inflammation, pain, arthritis, osteoporosis, multiple sclerosis, renal disease, and other autoimmune or inflammatory disorders dependent on the tissue invasion of leukocytes or other activated migrating cells. Additionally, the compounds of the present invention are useful in the treatment of acute and chronic neurodegenerative disorders including stroke, head trauma, spinal cord injury, Alzheimer's disease, amyotrophic lateral sclerosis, cerebral amyloid angiopathy, AIDS, Parkinson's disease, Huntington's disease, prion diseases, myasthenia gravis, and Duchenne's muscular dystrophy.

Gelatinase A and stromelysin-1 are members of the matrix metalloproteinase (MMP) family (Woessner J. F., *FASEB J.*, 1991;5:2145–2154) Other members include fibroblast collagenase, neutrophil collagenase, gelatinase B (92 kDa gelatinase), stromelysin-2, stromelysin-3, matrilysin, collagenase 3 (Freije J. M., Diez-Itza I., Balbin M., Sanchez L. M., Blasco R., Tolivia J., and Lopez-Otin C., *J. Biol. Chem.*, 1994;269:16766–16773), and the newly discovered membrane-associated matrix metalloproteinases (Sato H., Takino T., Okada Y., Cao J., Shinagawa A., Yamamoto E., and Seiki M., *Nature*, 1994;370:61–65).

The catalytic zinc in matrix metalloproteinases is a focal point for inhibitor design. The modification of substrates by introducing chelating groups has generated potent inhibitors such as peptide hydroxymates and thiol-containing peptides. Peptide hydroxamates and the natural endogenous inhibitors of MMPs (TIMPs) have been used successfully to treat animal models of cancer and inflammation.

The ability of the matrix metalloproteinases to degrade various components of connective tissue makes them potential targets for controlling pathological processes. For example, the rupture of an atherosclerotic plaque is the most common event initiating coronary thrombosis. Destabilization and degradation of the extracellular matrix surrounding these plaques by MMPs has been proposed as a cause of plaque fissuring. The shoulders and regions of foam cell accumulation in human atherosclerotic plaques show locally increased expression of gelatinase B, stromelysin-1, and interstitial collagenase. In situ zymography of this tissue revealed increased gelatinolytic and caseinolytic activity (Galis Z. S., Sukhova G. K., Lark M. W., and Libby P., "Increased expression of matrix metalloproteinases and matrix degrading activity in vulnerable regions of human atherosclerotic plaques," *J. Clin. Invest.*, 1994;94:2494–2503). In addition, high levels of stromelysin RNA message have been found to be localized to individual cells in atherosclerotic plaques removed from heart transplant patients at the time of surgery (Henney A. M., Wakeley P. R., Davies M. J., Foster K., Hembry R., Murphy G., and Humphries S., "Localization of stromelysin gene expression in atherosclerotic plaques by in situ hybridization," *Proc. Nat'l. Acad. Sci.*, 1991;88:8154–8158).

Inhibitors of matrix metalloproteinases will have utility in treating degenerative aortic disease associated with thinning of the medial aortic wall. Increased levels of the proteolytic activities of MMPs have been identified in patients with aortic aneurisms and aortic stenosis (Vine N. and Powell J. T., "Metalloproteinases in degenerative aortic diseases," *Clin. Sci.*, 1991;81:233–239).

Heart failure arises from a number of diverse etiologies, but a common characteristic is cardiac dilation, which has been identified as an independent risk factor for mortality (Lee T. H., Hamilton M. A., Stevenson L. W., Moriguchi J. D., Fonarow G. C., Child J. S., Laks H., and Walden J. A., "Impact of left ventricular size on the survival in advanced heart failure," *Am. J. Cardiol.*, 1993;72:672–676). This remodeling of the failing heart appears to involve the breakdown of extracellular matrix. Matrix metalloproteinases are increased in patients with both idiopathic and ischemic heart failure (Reddy H. K., Tyagi S. C., Tjaha I. E., Voelker D. J., Campbell S. E., and Weber K. T., "Activated myocardial collagenase in idiopathic dilated cardiomyopathy," *Clin. Res.*, 1993;41:660A; Tyagi S. C., Reddy H. K., Voelker D., Tjara I. E., and Weber K. T., "Myocardial collagenase in failing human heart," *Clin. Res.*, 1993;41:681A). Animal models of heart failure have shown that the induction of gelatinase is important in cardiac dilation (Armstrong P. W., Moe G. W., Howard R. J., Grima E. A., and Cruz T. F., "Structural remodeling in heart failure: gelatinase induction," *Can. J. Cardiol.*, 1994;10:214–220), and cardiac dilation precedes profound deficits in cardiac function (Sabbah H. N., Kono T., Stein P. D., Mancini G. B., and Goldstein S., "Left ventricular shape changes during the course of evolving heart failure," *Am. J. Physiol.*, 1992;263:H266–270).

Neointimal proliferation, leading to restenosis, frequently develops after coronary angioplasty. The migration of vascular smooth muscle cells (VSMCs) from the tunica media to the neointima is a key event in the development and progression of many vascular diseases and a highly predictable consequence of mechanical injury to the blood vessel (Bendeck M. P., Zempo N., Clowes A. W., Galardy R. E., and Reidy M., "Smooth muscle cell migration and matrix metalloproteinase expression after arterial injury in the rat," *Circulation Research*, 1994;75:539–545). Northern blotting and zymographic analyses indicated that gelatinase A was the principal MMP expressed and excreted by these cells. Further, antisera capable of selectively neutralizing gelatinase A activity also inhibited VSMC migration across basement membrane barrier. After injury to the vessel, gelatinase A activity increased more than 20-fold as VSMCs underwent the transition from a quiescent state to a proliferating, motile phenotype (Pauly R. R., Passaniti A., Bilato C., Monticone R., Cheng L., Papadopoulos N., Gluzband Y. A., Smith L., Weinstein C., Lakatta E., and Crow M. T., "Migration of cultured vascular smooth muscle cells through a basement membrane barrier requires type IV collagenase activity and is inhibited by cellular differentiation," *Circulation Research*, 1994;75:41–54).

Collagenase and stromelysin activities have been demonstrated in fibroblasts isolated from inflamed gingiva (Uitto V.

J., Applegren R., and Robinson P. J., "Collagenase and neutral metalloproteinase activity in extracts from inflamed human gingiva," *J. Periodontal Res.,* 1981;16:417–424), and enzyme levels have been correlated to the severity of gum disease (Overall C. M., Wiebkin O. W., and Thonard J. C., "Demonstrations of tissue collagenase activity in vivo and its relationship to inflammation severity in human gingiva," *J. Periodontal Res.,* 1987;22:81–88). Proteolytic degradation of extracellular matrix has been observed in corneal ulceration following alkali burns (Brown S. I., Weller C. A., and Wasserman H. E., "Collagenolytic activity of alkali burned corneas," *Arch. Ophthalmol.,* 1969;81:370–373). Thiol-containing peptides inhibit the collagenase isolated from alkali-burned rabbit corneas (Burns F. R., Stack M. S., Gray R. D., and Paterson C. A., *Invest. Ophthalmol.,* 1989;30:1569–1575).

Stromelysin is produced by basal keratinocytes in a variety of chronic ulcers (Saarialho-Kere U. K., Ulpu K., Pentland A. P., Birkedal-Hansen H., Parks W. O., and Welgus H. G., "Distinct Populations of Basal Keratinocytes Express Stromelysin-1 and Stromelysin-2 in Chronic Wounds," *J. Clin. Invest.,* 1994;94:79–88).

Stromelysin-1 mRNA and protein were detected in basal keratinocytes adjacent to but distal from the wound edge in what probably represents the sites of the proliferating epidermis. Stromelysin-1 may thus prevent the epidermis from healing.

Davies et al., (*Cancer Res.,* 1993;53:2087–2091) reported that a peptide hydroxymate, BB-94, decreased the tumor burden and prolonged the survival of mice bearing human ovarian carcinoma xenografts. A peptide of the conserved MMP propeptide sequence was a weak inhibitor of gelatinase A and inhibited human tumor cell invasion through a layer of reconstituted basement membrane (Melchiori A., Albili A., Ray J. M., and Stetler-Stevenson W. G., *Cancer Res.,* 1992;52:2353–2356). The natural tissue inhibitor of metalloproteinase-2 (TIMP-2) also showed blockage of tumor cell invasion in in vitro models (DeClerck Y.A, Perez N., Shimada H., Boone T. C., Langley K. E., and Taylor S. M., *Cancer Res.,* 1992;52:701–708). Studies of human cancers have shown that gelatinase A is activated on the invasive tumor cell surface (Strongin A. Y., Marmer B. L., Grant G. A., and Goldberg G. I., *J. Biol. Chem.,* 1993;268:14033–14039) and is retained there through interaction with a receptor-like molecule (Monsky W. L., Kelly T., Lin C.-Y., Yeh Y., Stetler-Stevenson W. G., Mueller S. C., and Chen W.-T., *Cancer Res.,* 1993;53:3159–3164).

Inhibitors of MMPs have shown activity in models of tumor angiogenesis (Taraboletti G., Garofalo A., Belotti D., Drudis T., Borsotti P., Scanziani E., Brown P. D., and Giavazzi R., *Journal of the National Cancer Institute,* 1995;87:293 and Benelli R., Adatia R., Ensoli B., Stetler-Stevenson W. G., Santi L., and Albini A, *Oncology Research,* 1994;6:251–257).

Several investigators have demonstrated consistent elevation of stromelysin and collagenase in synovial fluids from osteo- and rheumatoid arthritis patients as compared to controls (Walakovits L. A., Moore V. L., Bhardwaj N., Gallick G. S., and Lark M. W., "Detection of stromelysin and collagenase in synovial fluid from patients with rheumatoid arthritis and post-traumatic knee injury," *Arthritis Rheum.,* 1992;35:35–42; Zafarullah M., Pelletier J. P., Cloutier J. M., and Marcel-Pelletier J., "Elevated metalloproteinases and tissue inhibitor of metalloproteinase mRNA in human osteoarthritic synovia," *J. Rheumatol.,* 1993;20:693–697). TIMP-1 and TIMP-2 prevented the formation of collagen fragments, but not proteoglycan fragments in both the bovine nasal and pig articular cartilage models for arthritis, while a synthetic peptide hydroxamate could prevent the formation of both fragments (Andrews H. J., Plumpton T. A., Harper G. P., and Cawston T. E., *Agents Actions,* 1992;37:147–154; Ellis A. J., Curry V. A., Powell E. K., and Cawston T. E., *Biochem. Biophys. Res. Commun.,* 1994;201:94–101).

Gijbels et al., (*J. Clin. Invest,* 1994;94:2177–2182) recently described a peptide hydroxamate, GM6001, that suppressed the development or reversed the clinical expression of experimental autoimmune encephalomyelitis (EAE) in a dose dependent manner, suggesting the use of MMP inhibitors in the treatment of autoimmune inflammatory disorders such as multiple sclerosis.

A recent study by Madri has elucidated the role of gelatinase A in the extravasation of T-cells from the blood stream during inflammation (Ramanic A. M., and Madri J. A., "The Induction of 72-kDa Gelatinase in T Cells upon Adhesion to Endothelial Cells is VCAM-1 Dependent," *J. Cell Biology,* 1994;125:1165–1178). This transmigration past the endothelial cell layer is coordinated with the induction of gelatinase A and is mediated by binding to the vascular cell adhesion molecule-1 (VCAM-1). Once the barrier is compromised, edema and inflammation are produced in the CNS. Also, leukocytic migration across the blood-brain barrier is known to be associated with the inflammatory response in EAE. Inhibition of the metalloproteinase gelatinase A would block the degradation of extracellular matrix by activated T-cells that is necessary for CNS penetration.

These studies provide the basis for the expectation that an effective inhibitor of gelatinase A and/or stromelysin-1 would have value in the treatment of diseases involving disruption of extracellular matrix resulting in inflammation due to lymphocytic infiltration, inappropriate migration of metastatic or activated cells, or loss of structural integrity necessary for organ function.

Neuroinflammatory mechanisms are implicated in a broad range of acute and chronic neurodegenerative disorders, including stroke, head trauma, multiple sclerosis, and Alzheimer's disease, to name a few (McGeer E. G. and McGeer P. L., "Neurodegeneration and the immune system". In: Calne D. B., ed. Neurodegenerative Diseases, W. B. Saunders, 1994:277–300). Other disorders that may involve neuroinflammatory mechanisms include amyotrophic lateral sclerosis (Leigh P. N., "Pathogenic mechanisms in amyotrophic lateral sclerosis and other motor neuron disorders". In: Caine D. B., ed., Neurodegenerative Diseases, W. B. Saunders, 1994:473–88), cerebral amyloid angiopathy (Mandybur T. I. and Balko G., "Cerebral amyloid angiopathy with granulomatous angiitis ameliorated by steroid-cytoxan treatment," *Clin. Neuropharm.,* 1992;1 5:241–7), AIDS (Gendelman H. E. and Tardieu M., "Macrophages/microglia and the pathophysiology of CNS injuries in AIDS," *J. Leukocyte Biol.,* 1994;56:387–8), Parkinson's disease, Huntington's disease, prion diseases, and certain disorders involving the peripheral nervous system, such as myasthenia gravis and Duchenne's muscular dystrophy. Neuroinflammation, which occurs in response to brain injury or autoimmune disorders, has been shown to cause destruction of healthy tissue (Martin R., MacFarland H. F., and McFarlin D. E., "Immunological aspects of demyelinating diseases," *Annul Rev. Immunol.,* 1992;10:153–87; Clark R. K., Lee E. V., Fish C. J., et al., "Development of tissue damage, inflammation and resolution following stroke: an immunohistochemical and quantitative planimetric study," *Brain Res. Bull.*, 1993;31:565–72; Giulian D. and Vaca K., "Inflammatory glia mediate delayed neuronal damage after ischemia in the central nervous system," *Stroke*, 1993;24(Suppl 12):184–90; Patterson P. H., "Cytokines in Alzheimer's disease and multiple sclerosis," *Cur. Opinion Neurobiol.*, 1995;5:642–6; McGeer P. L., Rogers J., and McGeer E. G., "Neuroimmune mechanisms in Alzheimer disease pathogenesis," *Alzheimer Dis. Assoc. Disorders*, 1994;8:149–58; Martin R. and McFarland H. F., "Immunological aspects of experimental allergic encephalomyelitis and multiple sclerosis," *Crit. Rev. Clin. Lab. Sci.*, 1995;32:121–82; Rogers J., Webster S., Lue L. F., et al., "Inflammation and Alzheimer's disease pathogenesis". In: *Neurobiology of Aging*, 1996;17:681–686; Rothwell N. J. and Relton J. K., "Involvement of cytokines in acute neurodegeneration in the CNS," *Neurosci Biobehav. Rev.*, 1993;17:217–27). The pathological profiles and clinical courses of these disorders differ widely, but they all have in common the participation of immune/inflammatory elements in the disease process. In particular, many neurodegenerative disorders are characterized by large numbers of reactive microglia in postmortem brain samples, indicative of an active inflammatory process (McGeer E. G. and McGeer P. L., supra., 1994).

Increasing attention is being directed toward inflammatory mechanisms in Alzheimer's disease. Several lines of evidence support the involvement of neuroinflammation in Alzheimer's disease: 1) There is a significant increase in inflammatory markers in the Alzheimer brain, including acute phase reactants, cytokines, complement proteins, and MHC molecules (McGeer et al., supra., 1994; Rogers et al., supra.); 2) There is evidence that β-amyloid induces neurodegenerative changes primarily through interactions with inflammatory molecules, and that inflammation alone is sufficient to induce neurodegeneration (Rogers et al., supra); and 3) Growing epidemiological data indicate that anti-inflammatory therapy can delay the onset and slow the progression of Alzheimer's disease (McGeer P. L. and Rogers J., "Anti-inflammatory agents as a therapeutic approach to Alzheimer's disease," *Neurology*, 1992;42:447–9; Canadian Study of Health and Aging, "Risk factors for Alzheimer's disease in Canada," *Neurology*, 1994;44:2073–80; Lucca U., Tettamanti M., Forloni G., and Spagnoli A., "Nonsteroidal antiinflammatory drug use in Alzheimer's disease," *Biol. Psychiatry*, 1994;36:854–66; Hampel H. and Müller N., "Inflammatory and immunological mechanisms in Alzheimer's disease," *DN&P*, 1995;8:599–608; Breitner J. C. S., Gau B. A., Welsh K. A., et al., "Inverse association of anti-inflammatory treatments and Alzheimer's disease: Initial results of a co-twin control study," *Neurology*, 1994;44:227–32; Breitner J. C. S., Welsh K. A., Helms M. J., et al., "Delayed onset of Alzheimer's disease with nonsteroidal anti-inflammatory and histamine H2 blocking drugs," *Neurobiol. Aging*, 1995;16:523–30; Andersen K., Launer L. J., Ott A., Hoes A. W., Breteler M. M. B., and Hofman A., "Do nonsteroidal anti-inflammatory drugs decrease the risk for Alzheimer's disease? The Rotterdam Study," *Neurology*, 1995;45:1441–5; Rich J. B., Rasmusson D. X., Folstein M. F., et al., "Nonsteroidal anti-inflammatory drugs in Alzheimer's disease," *Neurology*, 1995;45:51–5; Aisen P. S., "Anti-inflammatory therapy for Alzheimer's disease," *Dementia*, 1995;9:173–82; Rogers et al., supra). Chronic use of nonsteroidal anti-inflammatory drugs (NSAIDs), most commonly for the treatment of rheumatoid arthritis, decreases the probability of developing Alzheimer's disease, and there is reason to believe that other anti-inflammatory agents may also be effective, although direct evidence for the efficacy of such treatments is lacking (Hamper and Müller, supra., 1995). Furthermore, virtually all of the currently available compounds, which include corticosteroids, NSAIDs, antimalarial drugs, and colchicine, have serious drawbacks that make them undesirable in the treatment of chronic disorders. Glucocorticoids, which are in wide clinical use as anti-inflammatory/immunosuppressive drugs, can be directly neurotoxic and also are toxic to systemic organs at moderate to high doses. NSAIDs have gastrointestinal and renal side effects that obviate long-term use in most people, and few of them cross the blood-brain barrier in significant amounts. The toxic properties of chloroquine compounds and colchicine also are well known. An anti-inflammatory drug that is well-tolerated by patients and that crosses the blood-brain barrier has significant advantages for the treatment of acute and chronic degenerative diseases of the central nervous system.

Normal kidney function is dependent on the maintenance of tissues constructed from differentiated and highly specialized renal cells which are in a dynamic balance with their surrounding extracellular matrix (ECM) components (Davies M. et al., "Proteinases and glomerular matrix turnover," *Kidney Int.*, 1992;41:671–678). Effective glomerular filtration requires that a semi-permeable glomerular basement membrane (GBM) composed of collagens, fibronectin, enactin, laminin and proteoglycans is maintained. A structural equilibrium is achieved by balancing the continued deposition of ECM proteins with their degradation by specific metalloproteinases (MMP). The MMP belong to a supergene family of zinc endopeptidases (Woessner J. F., "Matrix metalloproteinases and their inhibitors in connective tissue remodelling," *FASEB J.*, 1991;5:2145–2154). These proteins are first secreted as proenzymes and are subsequently activated in the extracellular space. These proteinases are in turn subject to counter balancing regulation of their activity by naturally occurring inhibitors referred to as TIMPs (tissue inhibitors of metalloproteinases).

Deficiency or defects in any component of the filtration barrier may have catastrophic consequences for longer term renal function. For example, in hereditary nephritis of Alport's type, associated with mutations in genes encoding ECM proteins, defects in collagen assembly lead to progressive renal failure associated with splitting of the GBM and eventual glomerular and interstitial fibrosis. By contrast in inflammatory renal diseases such as glomerulonephritis, cellular proliferation of components of the glomerulus often precede obvious ultrastructural alteration of the ECM matrix. Cytokines and growth factors implicated in proliferative glomerulonephritis such as interleukin-1, tumor necrosis factor, and transforming growth factor beta can upregulate metalloproteinase expression in renal mesangial cells (Martin J. et al., "Enhancement of glomerular mesangial cell neutral proteinase secretion by macrophages: role of interleukin 1," *J. Immunol.*, 1986;137:525–529; Marti H. P. et al., "Homology cloning of rat 72 kDa type IV collagenase: Cytokine and second-messenger inducibility in mesangial cells," *Biochem. J.*, 1993;291:441–446; Marti H. P. et al., "Transforming growth factor-b stimulates glomerular mesangial cell synthesis of the 72 kDa type IV collagenase," *Am. J Pathol.*, 1994;144:82–94). These metalloproteinases are believed to be intimately involved in the aberrant tissue remodeling and cell proliferation characteristic of renal diseases, such as, IgA nephropathy which can progress to through a process of gradual glomerular fibrosis and loss of functional GBM to end-stage renal disease. Metalloproteinase expression has already been well-characterized in experimental immune complex-mediated glomerulonephritis such as the anti-Thy 1.1 rat model (Bagchus W. M., Hoedemaeker P. J., Rozing J., Bakker W. W., "Glomerulonephritis induced by monoclonal anti-Thy 1.1 antibodies: A sequential histological and ultrastructural study in the rat," *Lab. Invest.*, 1986;55:680–687; Lovett D. H., Johnson R. J., Marti H. P., Martin J., Davies M., Couser W. G., "Structural characterization of the mesangial cell type IV collagenase and enhanced expression in a model of immune complex mediated glomerulonephritis," *Am. J. Pathol.*, 1992;141:85–98).

Unfortunately, at present, there are very limited therapeutic strategies for modifying the course of progressive renal disease. Although many renal diseases have an inflammatory component, their responses to standard immunosuppressive regimes are unpredictable and potentially hazardous to individual patients. The secondary consequences of gradual nephron failure such as activation of the renin-angiotensin system, accompanied by individual nephron glomerular hyperfiltration and renal hypertension, may be effectively treated with ACE inhibitors or angiotensin II receptor antagonists; but at best, these compounds can only reduce the rate of GFR decline.

A novel strategy to treat at least some renal diseases has been suggested by recent observations of MMP behavior. A rat mesangial cell MMP has been cloned (MMP-2) which is regulated in a tissue specific manner, and in contrast to other cellular sources such as tumor cell lines, is induced by cytokines (Brown P. D., Levy A. T., Margulies I., Liotta L. A., Stetler-Stevenson W. G., "Independent expression and cellular processing of Mr 72,000 type IV collagenase and interstitial collagenase in human tumorigenic cell lines," *Cancer Res.*, 1990;50:6184–6191; Marti H. P. et al., "Homology cloning of rat 72 kDa type IV collagenase: Cytokine and second-messenger inducibility in mesangial cells," *Biochem. J.*, 1993;291:441–446). While MMP-2 can specifically degrade surrounding ECM, it also affects the phenotype of adjacent mesangial cells. Inhibition of MMP-2 by antisense oligonucleotides or transfection techniques can induce a reversion of the proliferative phenotype of cultured mesangial cells to a quiescent or non-proliferative phenotype mimicking the natural in vitro behavior of these cells (Kitamura M. et al., "Gene transfer of metalloproteinase transin induces aberrant behaviour of cultured mesangial cells," *Kidney Int.*, 1994;45:1580–1586; Turck J. et al., "Matrix metalloproteinase 2 (gelatinase A) regulates glomerular mesangial cell proliferation and differentiation," *J. Biol. Chem.*, 1996;271:15074–15083).

Inhibitors of MMP (MMPi) clearly have potential clinical applications in a host of diseases characterized by disturbance of extracellular matrix-cell interactions resulting in abnormal tissue remodeling (Vincenti M. P. et al., "Using inhibitors of metalloproteinases to treat arthritis," *Arthritis Rheum.*, 1994;8:1115–1126; Grams F. et al., "X-ray structures of human neutrophil collagenase complexed with peptide hydroxyamate and peptide thiol inhibitors. Implications for substrate binding and rational drug design," *Eur. J. Biochem.*, 1995;228:830–841).

We have identified a series of tricyclic sulfonamide compounds and their derivatives that are inhibitors of matrix metalloproteinases, particularly collagenase-3, stromelysin-1 and gelatinase A, and thus useful as agents for the treatment of multiple sclerosis, atherosclerotic plaque rupture, restenosis, aortic aneurism, heart failure, left ventricular dilation, periodontal disease, corneal ulceration, treatment of burns, decubital ulcers, wound repair, cancer, inflammation, pain, arthritis, osteoporosis, renal disease, or other autoimmune or inflammatory diseases dependent upon tissue invasion by leukocytes or other activated migrating cells, acute and chronic neurodegenerative disorders including stroke, head trauma, spinal cord injury, Alzheimer's disease, amyotrophic lateral sclerosis, cerebral amyloid angiopathy, AIDS, Parkinson's disease, Huntington's diseases, prion diseases, myasthenic gravis, and Duchenne's muscular dystrophy.

SUMMARY OF THE INVENTION

Accordingly, a first aspect of the present invention is a compound of Formula I

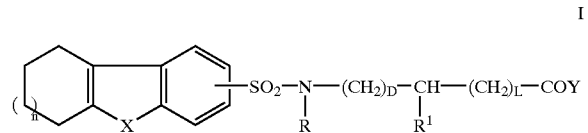

wherein
 n is zero or an integer of 1 or 2;
 X is —O—,
 —S(O)$_p$- wherein
 p is zero or an integer of 1 or 2,

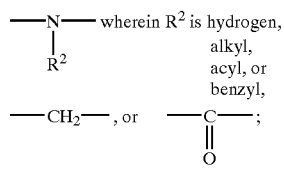

R is hydrogen,
 alkyl,
 hydroxyalkyl,
 alkoxyalkyl,
 trifluoromethyl,
 alkanoyloxyalkyl,
 alkanoylaminoalkyl,
 alkylthioalkyl,
 alkylsulfinylalkyl,
 alkylsulfonylalkyl,
 aminoalkyl,
 alkylaminoalkyl,
 dialkylaminoalkyl,
 N-alkylpiperazinoalkyl,
 N-phenylalkylpiperazinoalkyl,
 morpholinoalkyl,
 thiomorpholinoalkyl,
 piperidinoalkyl,
 pyrrolidinoalkyl,
 N-alkylalkylpiperidinolalkyl,
 pyridylalkyl,
 thienylalkyl,
 quinolinylalkyl,
 thiazolylalkyl,
 cycloalkyl,
 cycloalkylalkyl,
 phenyl,
 phenyl substituted by one to three substituents selected
  from the group
  consisting of:
   hydroxy,
   alkoxy, alkyl,
alkylthio,
alkylsulfinyl,
alkylsulfonyl,
amino,
alkylamino,
dialkylamino,
halogen,
cyano,
nitro,
trifluoromethyl or on adjacent carbon atoms by either a one to two carbon alkenylenedioxy group or a two to three carbon alkenyleneoxy group,
phenylalkyl,
phenylalkyl wherein phenyl is substituted by alkyl,
  alkoxy,
  halogen, or
  trifluoromethyl,
heteroaryl,
heteroaryl substituted by one to two substituents selected from the group consisting of:
  alkyl, or
  halogen,
biphenyl,
biphenyl substituted by alkyl,
  alkoxy,
  halogen,
  trifluoromethyl, or
  cyano,
biphenylalkyl or
biphenylalkyl wherein biphenyl is substituted by
  alkyl,
  alkoxy,
  halogen,
  trifluoromethyl, or
  cyano;
D is zero or an integer of 1 to 3;
L is zero or an integer of 1 to 3;
$R^1$ is hydrogen,
  a side chain of a natural amino acid or
  a side chain of an unnatural amino acid;
Y is $OR^3$ wherein $R^3$ is hydrogen,
  methyl,
  ethyl, or
  benzyl, or
NH—$OR^4$ wherein $R^4$ is hydrogen,
  alkyl, or
  benzyl;
and corresponding isomers thereof, or a pharmaceutically acceptable salt thereof.

As matrix metalloproteinase inhibitors, the compounds of Formula I are useful as agents for the treatment of multiple sclerosis. They are also useful as agents for the treatment of atherosclerotic plaque rupture, aortic aneurism, heart failure, left ventricular dilation, restenosis, periodontal disease, corneal ulceration, treatment of burns, decubital ulcers, wound repair, cancer metastasis, tumor angiogenesis, inflammation, pain, arthritis, osteoporosis, renal disease, and other autoimmune or inflammatory disorders dependent upon tissue invasion by leukocytes or other activated migrating cells, acute and chronic neurodegenerative disorders including stroke, head trauma, spinal cord injury, Alzheimer's disease, amyotrophic lateral sclerosis, cerebral amyloid angiopathy, AIDS, Parkinson's disease, Huntington's disease, prion diseases, myasthenia gravis, and Duchenne's muscular dystrophy.

A still further embodiment of the present invention is a pharmaceutical composition for administering an effective amount of a compound of Formula I in unit dosage form in the treatment methods mentioned above. Finally, the present invention is directed to methods for production of compounds of Formula I.

DETAILED DESCRIPTION OF THE INVENTION

In the compounds of Formula I, the term "alkyl" means a straight or branched hydrocarbon radical having from 1 to 6 carbon atoms and includes, for example, methyl, ethyl, n-propyl, isopropyl, n-butyl, sec-butyl, isobutyl, tert-butyl, n-pentyl, n-hexyl, and the like.

The term "alkenyl" means a straight or branched unsaturated hydrocarbon radical having from 2 to 6 carbon atoms and includes, for example, ethenyl, 2-propenyl, 1-butenyl, 2-butenyl, 1-pentenyl, 2-pentenyl, 3-methyl-3-butenyl, 1-hexenyl, 2-hexenyl, 3-hexenyl, and the like.

"Alkoxy" and "thioalkoxy" are O-alkyl or S-alkyl of from 1 to 6 carbon atoms as defined above for "alkyl".

The term "cycloalkyl" means a saturated hydrocarbon ring having 3 to 7 carbon atoms optionally containing an oxygen or sulfur atom and includes, for example, cyclopropyl, cyclobutyl, cyclopentyl, cyclohexyl, cycloheptyl, and the like.

The term "aryl" means an aromatic radical which is a phenyl group, a phenyl group substituted by 1 to 4 substituents selected from alkyl as defined above, alkoxy as defined above, thioalkoxy as defined above, hydroxy, halogen, trifluoromethyl, amino, alkylamino as defined above for alkyl, dialkylamino as defined above for alkyl, nitro, cyano, carboxy, guanidino, amidino, $SO_3H$, CHO,

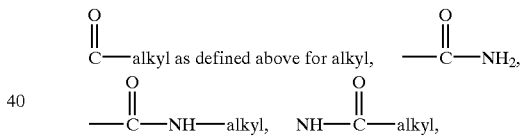

as defined above for alkyl,

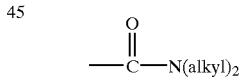

as defined above for alkyl, —$(CH_2)_n2$—$NH_2$ wherein $n^2$ is an integer of 1 to 5, —$(CH_2)_n2$—NH-alkyl as defied above for alkyl and $n^2$, —$(CH_2)_n2$—$N(alkyl)_2$ as defined above for alkyl and $n^2$,

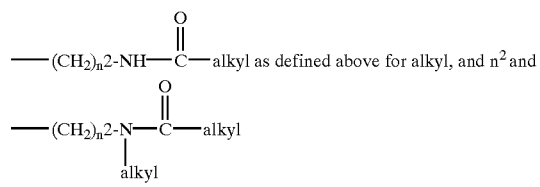

as defined above for alkyl and $n^2$.

The term "arylalkyl" means an aromatic radical attached to an alkyl radical wherein aryl and alkyl are as defined above for example benzyl, phenylethyl, 3-phenylpropyl, (4-chlorophenyl)methyl, and the like.

The term "acyloxymethyl" means a group of the formula

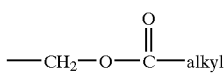

wherein alkyl is as defined above.

The term "heteroaryl" means a 5- and 6-membered heteroaromatic radical containing 1 to 3 heteroatoms selected from N, O, and S and includes, for example, a heteroaromatic radical which is 2- or 3-thienyl, 2- or 3-furanyl, 2- or 3-pyrrolyl, 2-, 3-, or 4-pyridinyl, 2-pyrazinyl, 2-, 4-, or 5-pyrimidinyl, 3- or 4-pyridazinyl, 1H-indol-6-yl, 1H-indol-5-yl, 1H-benzimidazol-6-yl, 1H-benzimidazol-5-yl, 2-, 4-, or 5-thiazolyl, 3-, 4-, or 5-isothiazolyl, 2-, 4-, or 5-imidazolyl, 3-, 4-, or 5-pyrazolyl, or 2- or 5-thiadiazolyl optionally substituted by a substituent selected from alkyl as defined above, alkoxy as defined above, thioalkoxy as defined above, hydroxy, halogen, trifluoromethyl, amino, alkylamino as defined above for alkyl, dialkylamino as defined above for alkyl, nitro, cyano, carboxy, guanidino, amidino, SO$_3$H, CHO,

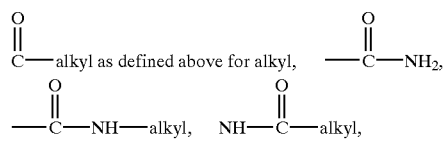

as defined above for alkyl,

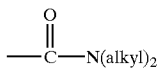

as defined above for alkyl, —(CH$_2$)$_n$2—NH$_2$ wherein n$^2$ is an integer of 1 to 5, —(CH$_2$)$_n$2—NH-alkyl as defined above for alkyl and n$^2$, —(CH$_2$)$_n$2—N(alkyl)$_2$ as defined above for alkyl and n$^2$,

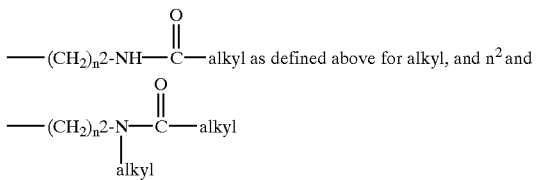

as defined above for alkyl and n$^2$.

The term "heterocycle" means a 3- to 7-membered cycloalkyl radical containing 1 to 3 heteroatoms selected from N, O, and S and includes, for example, 2- and 3-azetidinyl, 3- and 4-azetidinyl-2-one, 4- and 5-imidazolidinyl-2-one, 2,4-dioxo-imidazolidinyl, 2,4-dioxo-1,5,5-trimethyl-imidazolidinyl, 2-, 4-, and 5-thiazolidinyl, 4- and 5-oxazolidinyl-2-one, 2- and 3-tetrahydrofuranyl, 2- and 3-pyrrolidinyl, 2-, 3-, and 4-piperidinyl, 2- and 3-morpholinyl, 2- and 3-piperazinyl, 2-, 3-, and 4-azacycloheptanyl and the like.

The term "heteroarylalkyl" means a heteroaromatic radical attached to an alkyl radical wherein heteroaryl and alkyl are as defined above.

The term "heterocycloalkyl" means a heterocycle radical attached to an alkyl radical wherein heterocycle and alkyl are as defined above.

The term "pyrrolidinoalkyl" means a pyrrolidino group attached to an alkyl radical wherein alkyl is as defined above.

The term "pyridylalkyl" means a pyridyl group attached to an alkyl radical wherein alkyl is as defined above.

The term "thienylalkyl" means a thienyl group attached to an alkyl radical wherein alkyl is as defined above.

The term "quinolinylalkyl" means a quinolinyl group attached to an alkyl radical wherein alkyl is as defined above.

The term "thiazolylalkyl" means a thiazolyl group attached to an alkyl radical wherein alkyl is as defined above.

The term "phenylalkyl" means a phenyl group attached to an alkyl radical wherein alkyl is as defined above.

The term "biphenylalkyl" means a biphenyl group attached to an alkyl radical wherein alkyl is as defined above.

The term "acyl" means a group of the formula

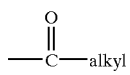

wherein alkyl is as defined above.

The term "hydroxyalkyl" means a hydroxy group attached to an alkyl radical wherein alkyl is as defined above.

The term "alkoxyalkyl" means an alkoxy group attached to an alkyl radical wherein alkoxy and alkyl are as defined above.

The term "aminoalkyl" means an amino group attached to an alkyl radical wherein alkyl is as defined above.

The term "morpholinoalkyl" means a morpholino group attached to an alkyl radical wherein alkyl is as defined above.

The term "thiomorpholinoalkyl" means a thiomorpholino group attached to an alkyl radical wherein alkyl is as defined above.

The term "piperidinoalkyl" means a piperidino group attached to an alkyl radical wherein alkyl is as defined above.

The term "cycloalkylalkyl" means a cycloalkyl group attached to an alkyl radical wherein cycloalkyl and alkyl are as defined above.

The terms "alkylaminoalkyl" and "dialkylaminoalkyl" are respectively alkyl-NH and (alkyl)$_2$N— wherein alkyl is as defined above.

The term "alkylamino" and "dialkylamino" are respectively alkyl NH— and (alkyl)$_2$N— wherein alkyl is or defined above.

The terms "alkylthioalkyl," "alkylsulfinylalkyl," and "alkylsulfonylalkyl" are respectively alkyl-S-alkyl, alkyl-SO-alkyl, and alkyl-SO$_2$-alkyl wherein alkyl is as defined above.

The terms "alkylthio," "alkylsulfinyl," and "alkylsulfonyl" are respectively alkyl-S—, alkyl-SO—, and alkyl-SO$_2$— wherein alkyl is as defined above.

The term "alkanoyloxyalkyl" means an

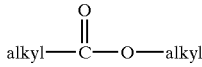

wherein alkyl is as defined above.

The term "alkanoylaminoalkyl" means an

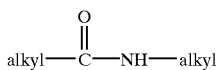

wherein alkyl is as defined above.
The term "N-alkylpiperazinoalkyl" means

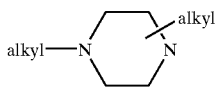

wherein alkyl is as defined above.
The term "N-phenylalkylpiperazinoalkyl" means

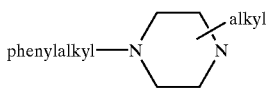

wherein alkyl is as defined above.
The term "N-alkylalkylpiperidinoalkyl" means

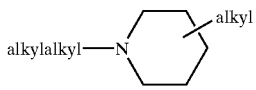

wherein alkyl is as defined above.
The term "alkenylenedioxy" means —O-alkyl-O— wherein alkyl is as defined above.
The term "alkenyleneoxy" means -alkyl-O— wherein alkyl is as defined above.
The term "side chain of a natural amino acid" (natural α amino acid) means the group Q in a natural amino acid of formula $H_2N$—CH(Q)—COOH. Examples of side chains of natural α amino acids include those of alanine, arginine, asparagine, aspartic acid, cysteine, glutamic acid, glycine, histidine, isoleucine, leucine, lysine, methionine, phenylalanine, proline, serine, threonine, tryptophan, tyrosine, and valine.

A natural α amino acid is an amino acid found in a living organism. Examples of such amino acids include glycine, alanine, valine, leucine, isoleucine, phenylalanine, proline, serine, threonine, tyrosine, asparagine, glutamine, lysine, arginine, tryptophan, histidine, cysteine, methionine, aspartic acid, and glutamic acid.

The functional groups in the amino acid side chains can be protected. For example, carboxyl groups can be esterified, amino groups can be converted to amides or carbamates, hydroxyl groups can be converted to ethers or esters, and thiol groups can be converted to thioethers or thioesters.

The term "side chain of an unnatural amino acid" means the group $R^{1a}$ in an unnaturally occurring amino acid of formula

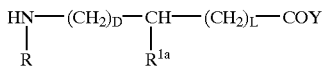

wherein
R is hydrogen
alkyl,
hydroxyalkyl,
alkoxyalkyl,
trifluoromethyl,
alkanoyloxyalkyl,
alkanoylaminoalkyl,
alkylthioalkyl,
alkylsulfinylalkyl,
alkylsulfonylalkyl,
aminoalkyl,
alkylaminoalkyl,
dialkylaminoalkyl,
N-alkylpiperazinoalkyl,
N-phenylalkylpiperazinoalkyl,
morpholinoalkyl,
thiomorpholinoalkyl,
piperidinoalkyl,
pyrrolidinoalkyl,
N-alkylalkylpiperidinoalkyl,
pyridylalkyl,
thienylalkyl,
quinolinylalkyl,
thiazolylalkyl,
cycloalkyl,
cycloalkylalkyl,
phenyl,
phenyl substituted by one to three substituents selected from the group consisting of:
  hydroxy,
  alkoxy,
  alkyl,
  alkylthio,
  alkylsulfinyl,
  alkylsulfonyl,
  amino,
  alkylamino,
  dialkylamino,
  halogen,
  cyano,
  nitro,
  trifluoromethyl or on adjacent carbon atoms by either a one to two carbon alkenylenedioxy group or a two to three carbon alkenyleneoxy group,
phenylalkyl,
phenylalkyl wherein phenyl is substituted by alkyl,
  alkoxy,
  halogen, or
  trifluoromethyl,
heteroaryl,
  heteroaryl substituted by one to two substituents selected from the group consisting of:
    alkyl, or
    halogen,
biphenyl,
biphenyl, substituted by alkyl,
  alkoxy,
  halogen,
  trifluoromethyl, or
  cyano,
biphenylalkyl or
biphenylalkyl wherein biphenyl is substituted by
  alkyl,
  alkoxy,
  halogen,
  trifluoromethyl, or
  cyano;

D is zero or an integer of 1 to 3;
L is zero or an integer of 1 to 3;
$R^{1a}$ is the side chain of an unnaturally occurring amino acid. Unnaturally occurring amino acids are well-known in the art, e.g., Roberts et al., "Unusual Amino Acids in Peptide Synthesis," *The Peptides*, 1993;5:341–429, but are not naturally found in living organisms. The side chains of unnatural amino acids include, but are not limited to:
hydrogen,
—$(CH_2)_n$-naphthalimide wherein n is zero or an integer of 1 to 2,
—$(CH_2)_n$-phthalimide wherein n is as defined above,
—$(CH_2)_n$-aryl wherein n is as defined below,
alkyl,
substituted alkyl wherein the substitutent is selected from the group consisting of:
SH,
$OR^5$ wherein $R^5$ is hydrogen, alkyl, phenyl, or benzyl,
$SR^5$ wherein $R^5$ is as defined above,
halogen,

wherein $R^5$ and $R^5a$ are either the same or different and each is the same as defined above for $R^5$,
$CO_2H$,
$COR^5$ wherein $R^5$ is as defined above,
CHO, or

wherein $R^5$ and $R^{5a}$ are either the same or different and each is the same as defined above for $R^5$,
aryl,
—$(CH_2)_n$-phenyl wherein n is as defined above,
alkenyl,
$(CH_2)_n$-heteroaryl wherein n is as defined above,
heteroaryl,
heterocycle,
—$(CH_2)_m$—NH—Z—$R^5$ wherein m is an integer of 1 to 6, Z is

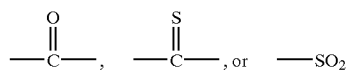

and $R^5$ is as defined above,
—$(CH_2)_m$—S—$C(phenyl)_3$ wherein m is as defined above,
—$(CH_2)_m$—O—$(CH_2)_L{}^a$-Phenyl wherein $L^a$ is an integer of 1 to 6 and
m is as defined above,

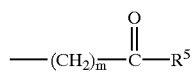

wherein m and $R^5$ are as defined above,

—$(CH_2)_m$—$NHSO_2$-aryl wherein m is as defined above,
—$(CH_2)_m$-cycloalkyl wherein m is as defined above,

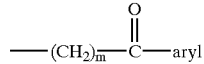

wherein m is as defined above,

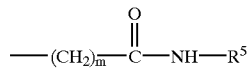

wherein m and $R^5$ are as defined above,

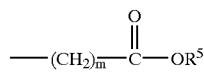

wherein m and $R^5$ are as defined above or

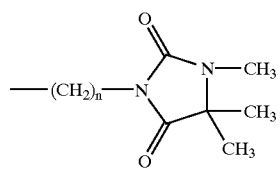

wherein n is as defined above; and
Y is $OR^3$ wherein $R^3$ is hydrogen,
methyl,
ethyl, or
benzyl, or
NH—$OR^4$ wherein $R^4$ is hydrogen,
alkyl, or
benzyl;
with the proviso that $R^{1a}$ is not the side chain of a natural α amino acid as defined above.

Additionally, side chains of natural α amino acids and unnatural amino acids having the D or R configuration are included within this term.

The functional groups in the amino acid side chains can be protected. For example, carboxyl groups can be esterified, amino groups can be converted to amides or carbamates, hydroxyl groups can be converted to ethers or esters, and thiol groups can be converted to thioethers or thioesters.

"Halogen" is fluorine, chlorine, bromine, or iodine.

"Alkali metal" is a metal in Group IA of the periodic table and includes, for example, lithium, sodium, potassium, and the like.

The acyloxymethyl esters of compounds of Formula I can be prepared by methods known to one skilled in the art. For example, the corresponding carboxylic acids can be allowed to react first with a suitable base to give the carboxylate anion, followed by reaction with a carboxylic halomethyl ester, which can be obtained from commercial suppliers or prepared by methods known to one skilled in the art, optionally in the presence of a suitable agent to activate the carboxylic halomethyl ester, which are known to one skilled in the art, to give the acyloxymethyl esters.

Some of the compounds of Formula I are capable of further forming both pharmaceutically acceptable acid addition and/or base salts. All of these forms are within the scope of the present invention.

Pharmaceutically acceptable acid addition salts of the compounds of Formula I include salts derived from nontoxic inorganic acids such as hydrochloric, nitric, phosphoric, sulfuric, hydrobromic, hydriodic, hydrofluoric, phosphorous, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, trifluoroacetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge S. M. et al., "Pharmaceutical Salts," *J. of Pharma. Sci.*, 1977;66:1).

The acid addition salts of said basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge S. M. et al., "Pharmaceutical Salts," *J. of Pharma Sci*, 1977;66:1).

The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

Certain of the compounds of the present invention possess one or more chiral centers and each center may exist in the R or S configuration. The present invention includes all diastereomeric, enantiomeric, and epimeric forms as well as the appropriate mixtures thereof. Additionally, the compounds of the present invention may exist as geometric isomers. The present invention includes all cis, trans, syn, anti, entgegen (E), and zusammen (Z) isomers as well as the appropriate mixtures thereof.

A preferred compound of Formula I is

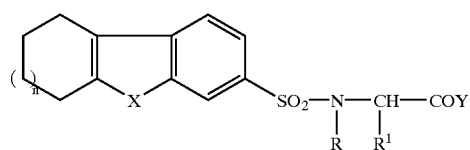

I wherein n, X, R, R$^1$, and Y are as defined above.

Another preferred compound of Formula I is

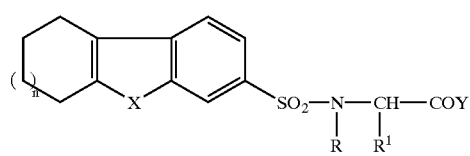

I wherein
  n is zero or an integer of 1; and
  X is —O—, or
    —CH$_2$—.

Another preferred compound of Formula I is

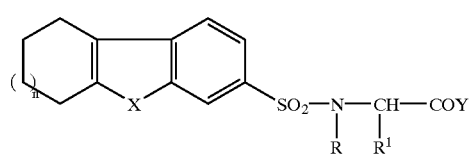

I wherein
  n is zero or an integer of 1;
  X is —O—, or
    —CH$_2$—; and
  R is hydrogen.

A more preferred compound of Formula I is

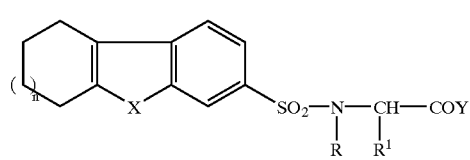

I wherein
  n is zero or an integer of 1;
  X is —O—, or
    —CH$_2$—;
  R is hydrogen; and
  Y is OH.

A most preferred compound of Formula I is

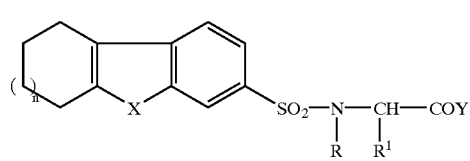

I wherein
n is zero or an integer of 1;
X is —O—, or
—CH$_2$—;
R is hydrogen; and
Y is NHOH.

Particularly valuable in this embodiment of the invention is a compound selected from the group consisting of:

(S) 3-Methyl-2-(6,7,8,9-tetrahydro-dibenzofuran-3-sulfonylamino)-butyric. acid;
(S) N-Hydroxy-3-methyl-2-(6,7,8,9-tetrahydro-dibenzofuran-3-sulfonylamino)-butyramide;
(S) 4-Phenyl-2-(6,7,8,9-tetrahydro-dibenzofuran-3-sulfonylamino)-butyric acid;
(S) 2-(6,7,8,9-Tetrahydro-dibenzofuran-3-sulfonylamino)-succinic acid;
(S) Phenyl-[(6,7,8,9-tetrahydro-dibenzofuran-3-sulfonylamino)]-acetic acid;
(S) 2-(6,7,8,9-Tetrahydro-dibenzofuran-3-sulfonylamino)-3-(3,4,4-trimethyl-2,5-dioxo-imidazolidin-1-yl)-propionic acid;
(S) 3-(1,3-Dioxo-1,3-dihydro-isoindol-2-yl)-2-(6,7,8,9-tetrahydro-dibenzofuran-3-sulfonylamino)-propionic acid;
(S) 2-(6,7,8,9-Tetrahydro-dibenzofuran-3-sulfonylamino)-4-(3,4,4-trimethyl-2,5-dioxo-imidazolidin-1-yl)-butyric acid;
(S) 2-(6,7,8,9-Tetrahydro-dibenzofuran-3-sulfonylamino)-5-(3,4,4-trimethyl-2,5-dioxo-imidazolidin-1-yl)-pentanoic acid;
(S) 5-Phenyl-2-(6,7,8,9-tetrahydro-dibenzofuran-3-sulfonylamino)-pentanoic acid;
(S) 4-Phenylmethanesulfinyl-2-(6,7,8,9-tetrahydro-dibenzofuran-3-sulfonylamino)butyric acid;
(S) 4-(1,3-Dioxo-1,3,dihydro-isoindol-2-yl)-2-(6,7,8,9-tetrahydro-dibenzofuran-3-sulfonylamino)-butyric acid;
(S) 5-(1,3-Dioxo-1,3-dihydro-isoindol-2-yl)-2-(6,7,8,9-tetrahydro-dibenzofuran-3-sulfonylamino)-pentanoic acid;
(S) 6-Phenyl-2-(6,7,8,9-tetrahydro-dibenzofuran-3-sulfonylamino)-hexanoic acid;
(S) 7-Phenyl-2-(6,7,8,9-tetrahydro-dibenzofuran-3-sulfonylamino)-heptanoic acid;
(S) 8-Phenyl-2-(6,7,8,9-tetrahydro-dibenzofuran-3-sulfonylamino)-octanoic acid;
(S) 4-Phenylsulfamoyl-2-(6,7,8,9-tetrahydro-dibenzofuran-3-sulfonylamino)-butyric acid;
(S) 4-Phenylmethanesulfonyl-2-(6,7,8,9-tetrahydro-dibenzofuran-3-sulfonylamino)-butyric acid;
(S) 4-Benzylsulfanyl-2-(6,7,8,9-tetrahydro-dibenzofuran-3-sulfonylamino)-butyric acid;
(S) 3-(1H-Indol-3-yl)-2-(6,7,8,9-tetrahydro-dibenzofuran-3-sulfonylamino)-propionic acid;
(S) 4-(1H-Indol-3-yl)-2-(6,7,8,9-tetrahydro-dibenzofuran-3-sulfonylamino)-butyric acid;
(S) 5-(1H-Indol-3-yl)-2-(6,7,8,9-tetrahydro-dibenzofuran-3-sulfonylamino)-pentanoic acid;
(S) 6-(1H-Indol-3-yl)-2-(6,7,8,9-tetrahydro-dibenzofuran-3-sulfonylamino)-hexanoic acid;
(S) 7-(1H-Indol-3-yl)-2-(6,7,8,9-tetrahydro-dibenzofuran-3-sulfonylamino)-heptanoic acid;
(S) 8-(1H-Indol-3-yl)-2-(6,7,8,9-tetrahydro-dibenzofuran-3-sulfonylamino)-octanoic acid;
(S) 2-(2,3-Dihydro-1H-8-oxa-cyclopenta[a]indene-6-sulfonylamino)-3-methyl-butyric acid;
(S) 3-Methyl-2-(6,7,8,9-tetrahydro-5H-10-oxa-benzo[a]azulene-2-sulfonylamino)-butyric acid;
(S) N-Hydroxy-4-phenyl-2-(6,7,8,9-tetrahydro-dibenzofuran-3-sulfonylamino)-butyramide;
(S) N-Hydroxy-3-(6,7,8,9-tetrahydro-dibenzofuran-3-sulfonylamino)-succinamic acid;
(S) N-Hydroxy-2-phenyl-2-(6,7,8,9-tetrahydro-dibenzofuran-3-sulfonylamino)-acetamide;
(S) N-Hydroxy-2-(6,7,8,9-tetrahydro-dibenzofuran-3-sulfonylamino)-3-(3,4,4-trimethyl-2,5-dioxo-imidazolidin-1-yl)-propionamide;
(S) 3-(1,3-Dioxo-1,3-dihydro-isoindol-2-yl)-N-hydroxy-2-(6,7,8,9-tetrahydro-dibenzofuran-3-sulfonylamino)-propionamide;
(S) N-Hydroxy-2-(6,7,8,9-tetrahydro-dibenzofuran-3-sulfonylamino)-4-(3,4,4-trimethyl-2,5-dioxo-imidazolidin-1-yl)-butyramide;
(S) 2-(6,7,8,9-Tetrahydro-dibenzofuran-3-sulfonylamino)-5-(3,4,4-trimethyl-2,5-dioxo-imidazolidin-1-yl)-pentanoic acid hydroxyamide;
(S) 5-Phenyl-2-(6,7,8,9-tetrahydro-dibenzofuran-3-sulfonylamino)-pentanoic acid hydroxyamide;
(S) N-Hydroxy-4-phenylmethanesulfinyl-2-(6,7,8,9-tetrahydro-dibenzofuran-3-sulfonylamino)-butyramide;
(S) 4-(1,3-Dioxo-1,3-dihydro-isoindol-2-yl)-N-hydroxy-2-(6,7,8,9-tetrahydro-dibenzofuran-3-sulfonylamino)-butyramide;
(S) 5-(1,3-Dioxo-1,3-dihydro-isoindol-2-yl)-2-(6,7,8,9-tetrahydro-dibenzofuran-3-sulfonylamino)-pentanoic acid hydroxyamide;
(S) 6-Phenyl-2-(6,7,8,9-tetrahydro-dibenzofuran-3-sulfonylamino)-hexanoic acid hydroxyamide;
(S) 7-Phenyl-2-(6,7,8,9-tetrahydro-dibenzofuran-3-sulfonylamino)-heptanoic acid hydroxyamide;
(S) 8-Phenyl-2-(6,7,8,9-tetrahydro-dibenzofuran-3-sulfonylamino)-octanoic acid hydroxyamide;
(S) 4Benzylsulfanyl-N-hydroxy-2-(6,7,8,9-tetrahydro-dibenzofuran-3-sulfonylamino)-butyramide;
(S) N-Hydroxy-4-phenylsulfamoyl-2-(6,7,8,9-tetrahydro-dibenzofuran-3-sulfonylamino)-butyramide;
(S) N-Hydroxy-4-phenylmethanesulfonyl-2-(6,7,8,9-tetrahydro-dibenzofuran-3-sulfonylamino)-butyramide;
(S) N-Hydroxy-3-(1H-indol-3-yl)-2-(6,7,8,9-tetrahydro-dibenzofuran-3-sulfonylamino)-propionamide;
(S) N-Hydroxy-4-(1H-indol-3-yl)-2-(6,7,8,9-tetrahydro-dibenzofuran-3-sulfonylamino)-butyramide;
(S) 5-(1H-Indol-3-yl)-2-(6,7,8,9-tetrahydro-dibenzofuran-3-sulfonylamino)-pentanoic acid hydroxyamide;
(S) 6-(1H-Indol-3-yl)-2-(6,7,8,9-tetrahydro-dibenzofuran-3-sulfonylamino)-hexanoic acid hydroxyamide;
(S) 7-(1H-Indol-3-yl)-2-(6,7,8,9-tetrahydro-dibenzofuran-3-sulfonylamino)-heptanoic acid hydroxyamide;
(S) 8-(1H-Indol-3-yl)-2-(6,7,8,9-tetrahydro-dibenzofuran-3-sulfonylamino)-octanoic acid hydroxyamide;
(S) 2-(2,3-Dihydro-1H-8-oxa-cyclopenta[a]indene-6-sulfonylamino)-N-hydroxy-3-methyl-butyramide;
(S) N-Hydroxy-3-methyl-2-(6,7,8,9-tetrahydro-5H-10-oxa-benzo[a]azulene-2-sulfonylamino)-butyramide;
(S) 3-Methyl-2-(6,7,8,9-tetrahydro-dibenzothiophene-3-sulfonylamino)-butyric acid;
(S) 3-Methyl-2-(9-methyl-6,7,8,9-tetrahydro-5H-carbazole-2-sulfonylamino)-butyric acid;
(S) 4Phenyl-2-(6,7,8,9-tetrahydro-dibenzothiophene-3-sulfonylamino)-butyric acid;
(S) 4Phenyl-2-(6,7,8,9-tetrahydro-5H-fluorene-2-sulfonylamino)-butyric acid;
(S) N-Hydroxy-4-phenyl-2-(6,7,8,9-tetrahydro-5H-fluorene-2-sulfonylamino)-butyramide;
(S) N-Hydroxy-3-methyl-2-(6,7,8,9-tetrahydro-dibenzothiophene-3-sulfonylamino)-butyramide;

(S) N-Hydroxy-3-methyl-2-(9-methyl-6,7,8,9-tetrahydro-5H-carbazole-2-sulfonylamino)-butyramide;
(S) N-Hydroxy-4-phenyl-2-(6,7,8,9-tetrahydro-dibenzothiophene-3-sulfonylamino)-butyramide;
(S) 3-Methyl-2-(6,7,8,9-tetrahydro-5H-fluorene-2-sulfonylamino)-butyric acid;
(S) N-Hydroxy-3-methyl-2-(6,7,8,9-tetrahydro-5H-fluorene-2-sulfonylamino)-butyramide;
(R) 3-Methyl-2-(6,7,8,9-tetrahydro-dibenzofuran-3-sulfonylamino)-butyric acid;
(R) N-Hydroxy-3-methyl-2-(6,7,8,9-tetrahydro-dibenzofuran-3-sulfonylamino)-butyramide;
(R) 4-Phenyl-2-(6,7,8,9-tetrahydro-dibenzofuran-3-sulfonylamino)-butyric acid;
(R) 2-(6,7,8,9-Tetrahydro-dibenzofuran-3-sulfonylamino)-succinic acid;
(R) Phenyl-[(6,7,8,9-tetrahydro-dibenzofuran-3-sulfonylamino)]-acetic acid;
(R) 2-(6,7,8,9-Tetrahydro-dibenzofuran-3-sulfonylamino)-3-(3,4,4-trimethyl-2,5-dioxo-imidazolidin-1-yl)-propionic acid;
(R) 3-(1,3-Dioxo-1,3-dihydro-isoindol-2-yl)-2-(6,7,8,9-tetrahydro-dibenzofuran-3-sulfonylamino)-propionic acid;
(R) 2-(6,7,8,9-Tetrahydro-dibenzofuran-3-sulfonylamino)-4-(3,4,4-trimethyl-2,5-dioxo-imidazolidin-1-yl)-butyric acid;
(R) 2-(6,7,8,9-Tetrahydro-dibenzofuran-3-sulfonylamino)-5-(3,4,4-trimethyl-2,5-dioxo-imidazolidin-1-yl)-pentanoic acid;
(R) 5-Phenyl-2-(6,7,8,9-tetrahydro-dibenzofuran-3-sulfonylamino)-pentanoic acid;
(R) 4-Phenylmethanesulfinyl-2-(6,7,8,9-tetrahydro-dibenzofuran-3-sulfonylamino)-butyric acid;
(R) 4-(1,3-Dioxo-1,3-dihydro-isoindol-2-yl)-2-(6,7,8,9-tetrahydro-dibenzofuran-3-sulfonylamino)-butyric acid;
(R) 5-(1,3-Dioxo-1,3dihydro-isoindol-2-yl)-2-(6,7,8,9-tetrahydro-dibenzofuran-3-sulfonylamino)-pentanoic acid;
(R) 6-Phenyl-2-(6,7,8,9-tetrahydro-dibenzofuran-3-sulfonylamino)-hexanoic acid;
(R) 7-Phenyl-2-(6,7,8,9-tetrahydro-dibenzofuran-3-sulfonylamino)-heptanoic acid;
(R) 8-Phenyl-2-(6,7,8,9-tetrahydro-dibenzofuran-3-sulfonylamino)-octanoic acid;
(R) 4-Phenylsulfamoyl-2-(6,7,8,9-tetrahydro-dibenzofuran-3-sulfonylamino)butyric acid;
(R) 4-Phenylmethanesulfonyl-2-(6,7,8,9-tetrahydro-dibenzofuran-3-sulfonylamino)-butyric acid;
(R) 4-Benzylsulfanyl-2-(6,7,8,9-tetrahydro-dibenzofuran-3-sulfonylamino)-butyric acid;
(R) 3-(1H-Indol-3-yl)-2-(6,7,8,9-tetrahydro-dibenzofuran-3-sulfonylamino)-propionic acid;
(R) 4-(1H-Indol-3-yl)-2-(6,7,8,9-tetrahydro-dibenzofuran-3-sulfonylamino)-butyric acid;
(R) 5-(1H-Indol-3-yl)-2-(6,7,8,9-tetrahydro-dibenzofuran-3-sulfonylamino)-pentanoic acid;
(R) 6-(1H-Indol-3-yl)-2-(6,7,8,9-tetrahydro-dibenzofuran-3-sulfonylamino)-hexanoic acid;
(R) 7-(1H-Indol-3-yl)-2-(6,7,8,9-tetrahydro-dibenzofuran-3-sulfonylamino)-heptanoic acid;
(R) 8-(1H-Indol-3-yl)-2-(6,7,8,9-tetrahydro-dibenzofuran-3-sulfonylamino)-octanoic acid;
(R) 2-(2,3-Dihydro-1H-8-oxa-cyclopenta[a]indene-6-sulfonylamino)-3-methyl-butyric acid;
(R) 3-Methyl-2-(6,7,8,9-tetrahydro-5H-10-oxa-benzo[a]azulene-2-sulfonylamino)-butyric acid;
(R) N-Hydroxy-4-phenyl-2-(6,7,8,9-tetrahydro-dibenzofuran-3-sulfonylamino)-butyramide;
(R) N-Hydroxy-3-(6,7,8,9-tetrahydro-dibenzofuran-3-sulfonylamino)-succinamic acid;
(R) N-Hydroxy-2-phenyl-2-(6,7,8,9-(tetrahydro-dibenzofuran-3-sulfonylamino)-acetamide;
(R) N-Hydroxy-2-(6,7,8,9-tetrahydro-dibenzofuran-3-sulfonylamino)-3-(3,4,4-trimethyl-2,5-dioxo-imidazolidin-1-yl)-propionamide;
(R) 3-(1,3-Dioxo-1,3-dihydro-isoindol-2-yl)-N-hydroxy-2-(6,7,8,9-tetrahydro-dibenzofuran-3-sulfonylamino)-propionamide;
(R) N-Hydroxy-2-(6,7,8,9-tetrahydro-dibenzofuran-3-sulfonylamino)-4-(3,4,4-trimethyl-2,5-dioxo-imidazolidin-1-yl)-butyramide;
(R) 2-(6,7,8,9-Tetrahydro-dibenzofuran-3-sulfonylamino)-5-3,4,4-trimethyl-2,5-dioxo-imidazolidin-1-yl)-pentanoic acid hydroxyamide;
(R) 5-Phenyl-2-(6,7,8,9-tetrahydro-dibenzofuran-3-sulfonylamino)-pentanoic acid hydroxyamide;
(R) N-Hydroxy-4-phenylmethanesulfinyl-2-(6,7,8,9-tetrahydro-dibenzofuran-3-sulfonylamino)-butyramide;
(R) 4-(1,3-Dioxo-1,3-dihydro-isoindol-2-yl)-N-hydroxy-2-(6,7,8,9-tetrahydro-dibenzofuran-3-sulfonylamino)-butyramide;
(R) 5-(1,3-Dioxo-1,3-dihydro-isoindol-2-yl)-2-(6,7,8,9-tetrahydro-dibenzofuran-3-sulfonylamino)-pentanoic acid hydroxyamide;
(R) 6-Phenyl-2-(6,7,8,9-tetrahydro-dibenzofuran-3-sulfonylamino)-hexanoic acid hydroxyamide;
(R) 7-Phenyl-2-(6,7,8,9-tetrahydro-dibenzofuran-3-sulfonylamino)-heptanoic acid hydroxyamide;
(R) 8-Phenyl-2-(6,7,8,9-tetrahydro-dibenzofuran-3-sulfonylamino)-octanoic acid hydroxyamide;
(R) 4-Benzylsulfanyl-N-hydroxy-2-(6,7,8,9-tetrahydro-dibenzofuran-3-sulfonylamino)-butyramide;
(R) N-Hydroxy-4-phenylsulfamoyl-2-(6,7,8,9-tetrahydro-dibenzofuran-3-sulfonylamino)-butyramide;
(R) N-Hydroxy-4-phenylmethanesulfonyl-2-(6,7,8,9-tetrahydro-dibenzofuran-3-sulfonylamino)-butyramide;
(R) N-Hydroxy-3-(1H-indol-3-yl)-2-(6,7,8,9-tetrahydro-dibenzofuran-3-sulfonylamino)-propionamide;
(R) N-Hydroxy-4-(1H-indol-3-yl)-2-(6,7,8,9-tetrahydro-dibenzofuran-3-sulfonylamino)-butyramide;
(R) 5-(1H-Indol-3-yl)-2-(6,7,8,9-tetrahydro-dibenzofuran-3-sulfonylamino)-pentanoic acid hydroxyamide;
(R) 6-(1H-Indol-3-yl)-2-(6,7,8,9-tetrahydro-dibenzofuran-3-sulfonylamino)-hexanoic acid hydroxyamide;
(R) 7-(1H-Indol-3-yl)-2-(6,7,8,9-tetrahydro-dibenzofuran-3-sulfonylamino)-heptanoic acid hydroxyamide;
(R) 8-(1H-Indol-3-yl)-2-(6,7,8,9-tetrahydro-dibenzofuran-3-sulfonylamino)-octanoic acid hydroxyamide;
(R) 2-(2,3-Dihydro-1H-8-oxa-cyclopenta[a]indene-6-sulfonylamino)-N-hydroxy-3-methyl-butyramide;
(R) N-Hydroxy-3-methyl-2-(6,7,8,9-tetrahydro-5H-10-oxa-benzo[a]azulene-2-sulfonylamino)-butyramide;
(R) 3-Methyl-2-(6,7,8,9-tetrahydro-dibenzothiophene-3-sulfonylamino)-butyric acid;
(R) 3-Methyl-2-(9-methyl-6,7,8,9-tetrahydro-5H-carbazole-2-sulfonylamino)-butyric acid;
(R) 4-Phenyl-2-(6,7,8,9-tetrahydro-dibenzothiophene-3-sulfonylamino)-butyric acid;
(R) 4-Phenyl-2-(6,7,8,9-tetrahydro-5H-fluorene-2-sulfonylamino)-butyric acid;
(R) N-Hydroxy-4-phenyl-2-(6,7,8,9-tetrahydro-5H-fluorene-2-sulfonylamino)butyramide;
(R) N-Hydroxy-3-methyl-2-(6,7,8,9-tetrahydro-dibenzothiophene-3-sulfonylamino)-butyramide;

(R) N-Hydroxy-3-methyl-2-(9-methyl-6,7,8,9-tetrahydro-5H-carbazole-2-sulfonylamino)-butyramide;
(R) N-Hydroxy-4-phenyl-2-(6,7,8,9-tetrahydro-dibenzothiophene-3-sulfonylamino)-butyramide;
(R) 3-Methyl-2-(6,7,8,9-tetrahydro-5H-fluorene-2-sulfonylamino)-butyric acid; and
(R) N-Hydroxy-3-methyl-2-(6,7,8,9-tetrahydro-5H-fluorene-2-sulfonylamino)-butyramide;
and corresponding isomers thereof; or a pharmaceutically acceptable salt thereof.

The compounds of Formula I are valuable inhibitors of a number of different matrix metalloproteinases. It has been shown previously that inhibitors of matrix metalloproteinases have efficacy in models of disease states like arthritis and metastasis that depend on modification of the extracellular matrix.

In vitro experiments were carried out which demonstrate the efficacy of compounds of Formula I as potent and specific inhibitors of a variety of matrix metalloproteinases. Experiments were carried out with the full-length and catalytic domains of the proteinases. Table 1 shows the activity of Examples 1–4 versus MMP-1FL (collagenase-1 full length enzyme), MMP-2CD (gelatinase A catalytic domain), MMP-2FL (gelatinase A full length enzyme), MMP-3CD (stromelysin-1 catalytic domain), MMP-7FL (matrilysin full length enzyme), MMP-9-FL (gelatinase B full length enzyme), MMP-13CD (collagenase-3 catalytic domain), and MMP-14CD (membrane-type MMP-1). $IC_{50}$ values were determined using a thiopeptolide substrate, Ac-Pro-Leu-Gly-thioester-Leu-Leu-Gly-OEt (Ye Q.-Z., Johnson L. L., Hupe D. J., and Baragi V., "Purification and Characterization of the Human Stromelysin Catalytic Domain Expressed in *Escherichia coli*," *Biochemistry*, 1992;31:11231–11235; Ye Q.-Z., Johnson L. L., Yu A. E., and Hupe D., "Reconstructed 19 kDa catalytic domain of gelatinase A is an active proteinase," *Biochemistry*, 1995;34:4702–4708.) MMP-13CD was expressed from a synthetic gene and purified from *Escherichia coli* cell culture according to a previously described method (Ye Q.-Z., Johnson L. L., and Baragi V., "Gene synthesis and expression in *E. coli* for PUMP, a human matrix metalloproteinase," *Biochemical and Biophysical Research Communications*, 1992; 186:143–149).

| | |
|---|---|
| MMP | Matrix metalloproteinase |
| TIMPs | Tissue inhibitors of matrix metalloproteinases |
| VSMC | Vascular smooth muscle cell |
| TFA | Trifluoroacetic acid |
| $IC_{50}$ | Concentration of compound required to inhibit 50% of enzyme activity |
| HCl | Hydrogen chloride |
| THF | Tetrahydrofuran |
| Pd | Palladium |
| Na | Sodium |
| NaH | Sodium hydride |
| LiOH | Lithium hydroxide |
| LiCl | Lithium Chloride |
| $H_2O$ | Water |
| $H_2$ | Hydrogen |
| CDI | 1,1'-Carbonyldiimidazole |
| Hv | light |
| $SO_3$.DMF | Sulfur trioxide dimethyl formamide |
| $SOCl_2$ | Thionyl Chloride |
| t-Bu | tertiary butyl |
| BOC | tertiary butoxycarbonyl |
| LDA | Lithium diisopropylamide |
| MeOH | Methanol |
| DMF | Dimethylformamide |
| p-TsOH(p-TSA) | para-Toluenesulfonic acid |
| $CHCl_3$ | Chloroform |
| $CDCl_3$ | Deuterated chloroform |
| E | Entgegen |
| Z | Zusammen |
| $H_2NOBz$ | O-Benzyl hydroxylamine |
| TEA | Triethylamine |
| $CH_3CN$ | Acetonitrile |
| DBU | 1,8-Diazabicyclo[5.4.0]undec-7-ene |
| DCC | Dicyclohexylcarbodiimide |
| PPA | Polyphosphoric acid |
| $BaSO_4$ | Barium sulfate |
| DMSO-$d_6$ | Deuterated dimethylsulfoxide |
| $MgSO_4$ | Magnesium sulfate |
| $^1H$-NMR | Proton nuclear magnetic resonance |
| PPM | Parts per million |
| MS | Mass spectrum |

Tricyclic aryl and tricyclic heteroaryl starting materials of formula (3)

TABLE 1

Biological Activity of Compounds of Formula I $IC_{50}$ (μM)

| Example | MMP-1FL | MMP-2CD | MMP-2FL | MMP-3CD | MMP-7FL | MMP-9FL | MMP-13CD | MMP-14CD |
|---|---|---|---|---|---|---|---|---|
| 1 | 6.7 | 0.037 | 0.335 | 0.046 | 82 | 30 | 3.45 | 0.38 |
| 2 | 6.05 | 0.034 | 0.43 | 0.0245 | 7.5 | 100 | 2.3 | 0.155 |
| 3 | 16 | 0.0167 | 0.45 | 0.0056 | 3.2 | 100 | 0.97 | 0.048 |
| 4 | 25 | 0.018 | 0.15 | 0.0215 | 2.3 | 28 | 1.345 | 0.064 |

The following list contains abbreviations and acronyms used within the schemes and text:

| | |
|---|---|
| GBM | Glomerular basement membrane |
| ECM | Extracellular matrix |
| CNS | Central nervous system |
| $CH_2Cl_2$ | Dichloromethane |
| EAE | Experimental autoimmune encephalomyelitis |

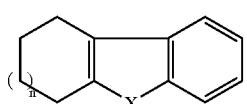

(3)

wherein n is zero or an integer of 1 or 2; and

X is —O—,
—S—,

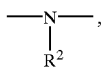

wherein
R² is hydrogen,
alkyl,
acyl, or
benzyl,
are either obtained from commercial sources (X=N—R² wherein R² is as defined above) or prepared using methods known in the art, e.g., Bachelet J. P. and Caubere P., *J. Org. Chem.*, 1982;47:234–238; Ebel F., *Helv. Chim. Acta*, 1929;12:3–16; Vanrysselberghe V. et al., *Ind. Eng. Chem. Res.*, 1996;35:3311–3318; Derouane D. et al., *J. Chem. Soc., Chem. Commun.*, 1995;10:993–994; Miki Y. and Sugimoto Y., *Seikiyu Gakkaishi*, 1994;37:386–394; Miki Y. et al., *Seikiyu Gakkaishi*, 1992;35:332–338; Rankel L. A., *Fuel Sci. Technol. Int.*, 1991;9:1435–1447; Siskin M. et al., *Energy Fuels*, 1990;4:482–488; Sundaram K. M. et al., *Chem. Eng. Commun.*, 1988;71:53–71; Francisco M. A. et al., *J. Org. Chem.*, 1988;53:596–600; Nagai M. et al., *J. Catal.*, 1986;97:52–58; Miyake M. et al., *Bull. Chem. Soc. Japan*, 1979;52:559–563; Ando W. et al., *J. Chem. Soc. Chem. Commun.*, 1975;17:704–705; Fraser P. S. et al., *J. Org. Chem.*, 1974;39:2509–2513; Cagniant P. et al., *Bull. Soc. Chim. Fr.*, 1969;2:607–612; and Cagniant D. et al., *Bull. Soc. Chim. Fr.*, 1969;2:601–606; U.S. Pat. Nos. 5,721,185, 5,670,680; International Published Patent Application WO 95/27717; Smith W. et al., J. Org. Chem., 1990;55:5301–5302; Mejer S., *Pol. of Chem.*, 1979;53:2385–2388; Canonne P. et al., *J. Org. Chem.*, 1980;45:1828–1835; Parham W. E., *Synthesis*, 1976;116–117; Japanese Patent Application JP 08191063 A2; Parhan W. E., *J. Org. Chem.*, 1969;34:1899–1904; McClure K. F. et al., *Bioorg. Med. Chem. Lett.*, 1998;8:143–146.

The synthesis of starting materials for a compound of Formula I wherein X is —O— is shown in Scheme 1. Thus, a compound of formula (1) wherein n is zero or an integer of 1 or 2 is reacted with phenol in the presence of sodium, or sodium hydride and the like in the presence of a solvent such as benzene, tetrahydrofuran and the like to afford a compound of formula (2). Cyclization of a compound of formula (2) in the presence of an acid such as, for example, polyphosphoric acid, para-toluenesulfonic acid and the like in the presence of a solvent such as benzene and the like affords a compound of formula (3).

The synthesis of compounds of Formula Ia, Ib, Ic, and Id are shown in Scheme 2. Thus, a compound of formula (3) wherein n is as defined above is sulfonated using a sulfonating reagent such as, for example, SO₃-DMF, and the like by refluxing in a solvent such as, for example, dichloroethane and the like to afford a compound of formula (4) wherein n is as defined above. A compound of formula (4) is chlorinated with a chlorinating reagent such as, for example, thionyl chloride and the like at about room temperature to afford a compound of formula (5) wherein n is as defined above. A compound of formula (5) is reacted with an amino acid of formula (6) wherein R¹ is hydrogen, a side chain of a natural amino acid or a side chain of an unnatural amino acid in the presence of a base such as, for example, triethylamine and the like in a solvent such as, for example, tetrahydrofuran/water and the like at about room temperature to afford a compound of Formula Ia wherein n and R¹ are as defined above. Alternatively, a compound of formula (5) is reacted with a C-protected amino acid of formula (7) wherein R¹ is as defined above in the presence of a base such as, for example, triethylamine and the like in the presence of a solvent such as, for example, dichloromethane and the like to afford a compound of formula (8) wherein n and R¹ are as defined above. A compound of formula (8) can be deprotected in the presence of an acid such as, for example, trifluoroacetic acid and the like, and a solvent such as, for example, dichloromethane and the like at about room temperature to afford a compound of Formula Ia. Coupling the acid chloride of Formula Ia with O-benzyl hydroxylamine in a solvent such as, for example, tetrahydrofuran and the like at about −10° C. to about 40° C. to afford a compound of Formula Ic wherein n and R¹ are as defined above. Reaction of a compound of Formula Ic with hydrogen gas in the presence of a catalyst such as, for example, palladium on barium sulfate and the like in a solvent such as, for example, methanol, tetrahydrofuran and the like to afford a compound of Formula Id wherein n and R¹ are as defined above. Reaction of a compound of formula (8) with a compound of formula R-Hal wherein
R is hydrogen,
alkyl,
hydroxyalkyl,
alkoxyalkyl,
trifluoromethyl,
alkanoyloxyalkyl,
alkanoylaminoalkyl,
alkylthioalkyl,
alkylsulfinylalkyl,
alkylsulfonylalkyl,
aminoalkyl,
alkylaminoalkyl,
dialkylaminoalkyl,
N-alkylpiperazinoalkyl,
N-phenylalkylpiperazinoalkyl,
morpholinoalkyl,
thiomorpholinoalkyl,
piperidinoalkyl,
pyrrolidinoalkyl,
N-alkylalkylpiperidinoalkyl,
pyridylalkyl,
thienylalkyl,
quinolinylalkyl,
thiazolylalkyl,
cycloalkyl,
cycloalkylalkyl,
phenyl,
phenyl substituted by one to three substituents selected from the group consisting of:
  hydroxy,
  alkoxy,
  alkyl,
  alkylthio,
  alkylsulfinyl,
  alkylsulfonyl, amino,
alkylamino,
dialkylamino,
halogen,
cyano,
nitro,
trifluoromethyl or on adjacent carbon atoms by either a
one to two carbon alkenylenedioxy group or a two to
three carbon alkenyleneoxy group,
phenylalkyl,
phenylalkyl wherein phenyl is substituted by alkyl,
alkoxy,
halogen, or
trifluoromethyl,
heteroaryl,
heteroaryl substituted by one to two substituents
selected from the group consisting of:
alkyl, or
halogen,
biphenyl,
biphenyl, substituted by alkyl,
alkoxy,
halogen,
trifluoromethyl, or
cyano,
biphenylalkyl or
biphenylalkyl wherein biphenyl is substituted by
alkyl,
alkoxy,
halogen,
trifluoromethyl, or
cyano;
and Hal is chlorine, bromine, or iodine in the presence of a base such as, for example, DBU and the like in a solvent such as, for example, acetonitrile and the like to afford a compound of formula (9) wherein n, R, and $R^1$ are as defined above. Reaction of a compound of formula (9) with an acid such as, for example, trifluoroacetic acid and the like in the presence of a solvent such as, for example, dichloromethane affords a compound of Formula Ib wherein n, R, and $R^1$ are as defined above.

The previous methodology can be applied to both natural and unnatural α-amino acids of formulas (6) and (7) which are readily available from commercial sources or can be prepared by methods known in the art. Alternatively, natural and unnatural α-amino acids of formulas (6) and (7) can be prepared as shown in Scheme 3. Thus employing the method of Evans D. A. et al., *J. Amer. Chem. Soc.*, 1982;104:1737–1739, N-Boc-glycine of formula (10) is coupled with the chiral sodium salt of benzyl oxazolidine of formula (11) in the presence of a coupling reagent such as, for example, carbonyldiimidazole in a solvent such as, for example, tetrahydrofuran and the like at about –10° C. to about room temperature to afford the compound of formula (12). The enolate of the compound of formula (12) is formed by reaction with lithium diisopropylamide and subsequently alkylated with a compound of formula

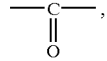

wherein $R^1$ and Hal are as defined above to afford a compound of formula (13) as a mixture of diastereomers. The diastereomers are separated using chromatography using an absorbent such as, for example, silica gel and the like to afford pure diastereomers. The pure diastereomers are treated with gaseous hydrogen chloride in a solvent such as dichloromethane and the like at about room temperature to afford a compound of formula (14) wherein $R^1$ is as defined above. Reaction of a compound of formula (14) with a compound of formula $Ar\ SO_2Cl$ wherein Ar is

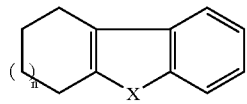

wherein
X is —O—,
—S(O)p— wherein p is zero or an integer of 1 or 2,

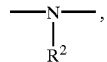

wherein
$R^2$ is hydrogen,
alkyl,
acyl, or
benzyl,
—CH$_2$—, or $$-\underset{\underset{O}{\|}}{C}-,$$

and n is as defined above (prepared by methodology described previously for preparing a compound of formula (5) from a compound of formula (3)) in the presence of a base such as, for example, triethylamine and the like, in a solvent mixture such as, for example, tetrahydrofuran and water at about 10° C. to about room temperature to afford a compound of formula (15) wherein $R^1$ is as defined above. The oxazolidone chiral auxiliary is removed by hydrolysis with a base such as, for example, lithium hydroxide and the like, in a solvent mixture such as, for example, dioxane/water at about room temperature to afford a compound of Formula Ie wherein $R^1$ is as defined above.

Scheme 4 shows the preparation of a compound of Formula If using the methodology of Myers A. G. et al., *Tetrahedron Lett.*, 1995;36:4555–4558. Thus, the enantiomeric pseudoephedrine glycinamide of formula (16) or its enantiomer is added to a slurry of lithium chloride and lithium diisopropylamide in a solvent such as, for example, tetrahydrofuran at about –78° C. to afford an O,N-dianion which is warmed to about 0° C. and treated with a compound of formula $R^1$-Hal wherein $R^1$ and Hal are as defined above to afford a compound of formula (17) wherein $R^1$ is as defined above having a high degree of diastereoselectivity (>99% de). A compound of formula (17) is treated with a compound of formula ArSO$_2$Cl wherein Ar is as defined above in the presence of a base such as, for example, triethylamine and the like in a solvent such as, for example, tetrahydrofuran/water at about 10° C. to about room temperature to afford a compound of formula (18) wherein Ar and $R^1$ are as defined above. The chiral auxiliary is then removed by hydrolysis with a base such as, for example, aqueous sodium hydroxide or water/methanol mixtures at about reflux to afford a compound of Formula If wherein Ar and $R^1$ are as defined above. Alternatively, the hydrolysis can be carried out by refluxing an aqueous solution of a compound of formula (18) without additional base being added.

Compounds of formula R-Hal or $R^1$-Hal are either commercially available or can be obtained by methods known in the art.

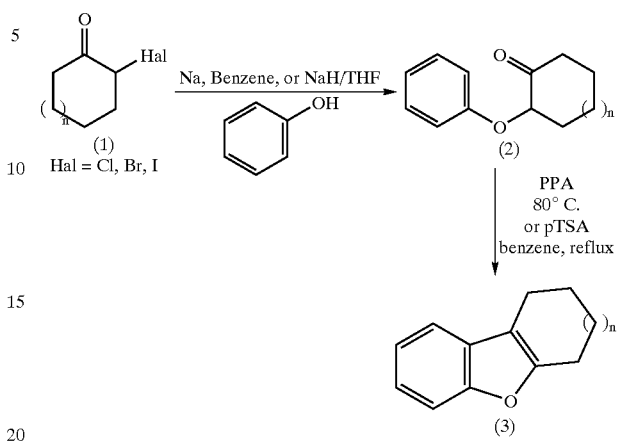

Scheme 1

Scheme 2

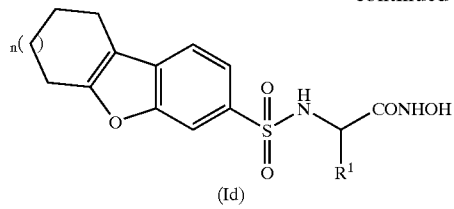

(Id)

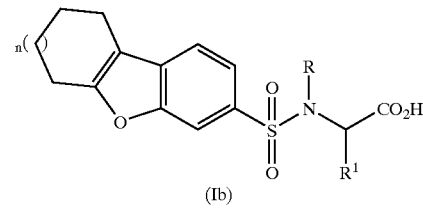

(Ib)

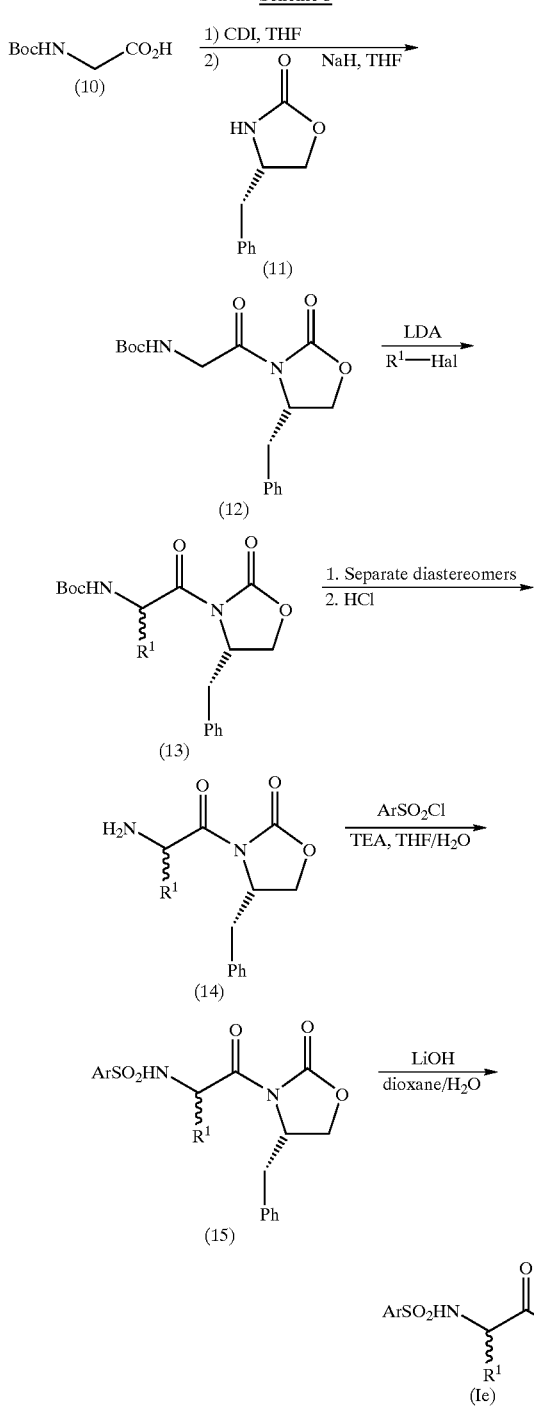

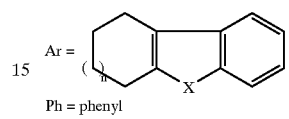

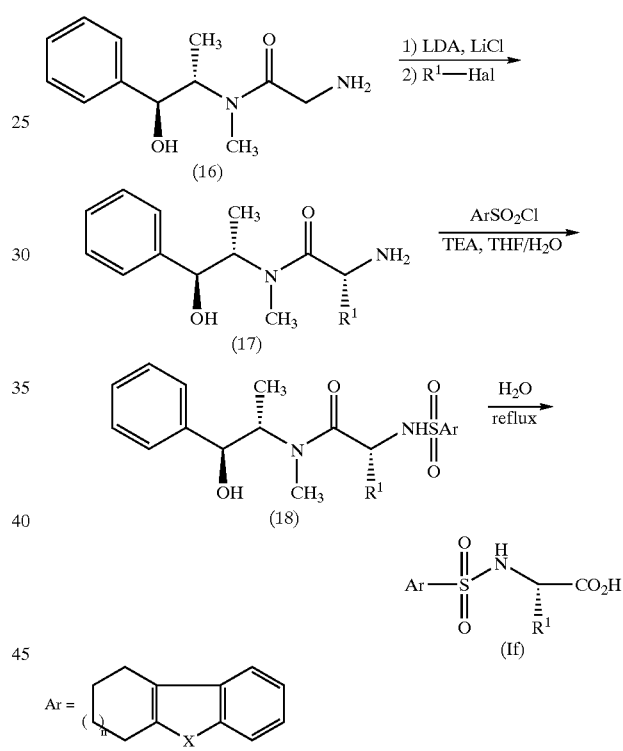

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Also, the compounds of the present invention can be administered by inhalation, for example, intranasally. Additionally, the compounds of the present invention can be administered transdermally. It will be obvious to those skilled in the art that the following dosage forms may comprise as the active component, either a compound of Formula I or a corresponding pharmaceutically acceptable salt of a compound of Formula I.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from 5 or 10 to about 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component, with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizing, and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 1 mg to 1000 mg, preferably 10 mg to 100 mg according to the particular application and the potency of the active component. The composition can, if desired, also contain other compatible therapeutic agents.

In therapeutic use as agents for the treatment of multiple sclerosis, atherosclerotic plaque rupture, aortic aneurism, heart failure, left ventricular dilation, restenosis, periodontal disease, corneal ulceration, treatment of burns, decubital ulcers, wound healing, cancer, inflammation, pain, arthritis, osteoporosis, renal disease, or other autoimmune or inflammatory disorders dependent upon tissue invasion by leukocytes, or other activated migrating cells, acute and chronic neurodegenerative disorders including stroke, head trauma, spinal cord injury, Alzheimer's disease, amyotrophic lateral sclerosis, cerebral amyloid angiopathy, AIDS, Parkinson's disease, Huntington's disease, prion diseases, myasthenia gravis, and Duchenne's muscular dystrophy, the compounds utilized in the pharmaceutical methods of the invention are administered at the initial dosage of about 1 mg to about 100 mg per kilogram daily. A daily dose range of about 25 mg to about 75 mg per kilogram is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstance is reached. For convenience, the total daily dosage may be divided and administered in portions during the day if desired.

The following nonlimiting examples illustrate the inventors' preferred methods for preparing the compounds of the invention.

EXAMPLE 1

(R) 3-Methyl-2-(6,7,8,9-tetrahydro-dibenzofuran-3-sulfonylamino)-butyric acid

Step (a) Preparation of 6,7,8,9-Tetrahydro-dibenzofuran-3-sulfonic acid

To a solution of tetrahydrodibenzofuran (4 g, 0.023 mol) in dichloroethane (50 mL) was added, in one portion, sulfur dioxide-DMF complex (6 g, 0.039 mol). The reaction mixture was refluxed for 14 hours, cooled, and concentrated in vacuo. The resulting crude liquid was dissolved in warm diethyl ether/ethanol yielding a precipitate on cooling. The solid was collected by filtration, washed with diethyl ether, and dried in vacuo to give the title compound as a pink solid (2.3 g, 40%).

$^1$HNMR (CDCl$_3$) δ7.9 (s, 1H), 7.7 (d, 1H), 7.4 (d, 1H), 2.8 (m, 2H), 2.6 (m, 2H), 2.0–1.8 (m, 4H) ppm.

Step (b) Preparation of 6,7,8,9-Tetrahydro-dibenzofuran-3-sulfonyl chloride 6,7,8,9-Tetrahydrodibenzofuran-3-sulfonic acid (2.1 g, 8.3 mmol) was suspended in thionyl chloride (25 mL) and stirred at room temperature for 6 hours. The solution was concentrated in vacuo, and the resulting liquid was taken up in ethyl acetate, washed with water, brine, and dried over magnesium sulfate. The solvent was concentrated to dryness, and the crude product was triturated with hexane and collected by filtration to give the sulfonyl chloride as a tan solid (1.3 g, 58%).

$^1$HNMR (CDCl$_3$) δ8.0 (s, 1H), 7.8 (d, 1H), 7.5 (d, 1H), 2.8 (m, 2H), 2.6 (m, 2H), 1.9–1.7 (m, 4H) ppm.

Step (c) Preparation of (R) 3-Methyl-2-(6,7,8,9-tetrahydro-dibenzofuran-3-sulfonylamino)-butyric acid, tert-butyl ester To a solution of (D)-valine, tert-butyl ester (0.13 g, 0.74 mmol) and triethylamine (0.075 g, 0.74 mmol) in tetrahydrofuran/water (5 mL, 1:1) was added in one portion at room temperature 6,7,8,9-tetrahydro-dibenzofuran-3-sulfonyl chloride (0.20 g, 0.74 mmol). The reaction mixture was stirred at room temperature for 14 hours, followed by the addition of aqueous HCl (1 M, 5 mL) and ethyl acetate (10 mL). The organic phase was separated and washed with brine, dried (MgSO$_4$), and concentrated to dryness to give the title compound as a white solid (0.24 g, 80%).

$^1$HNMR (CDCl$_3$) δ7.9 (s, 1H), 7.7 (d, 1H), 7.5 (d, 1H), 5.1 (d, 1H), 3.6 (dd, 1H), 2.8 (m, 2H), 2.6 (m, 2H), 2.0 (m, 1H), 1.9–1.8 (m, 4H), 1.1 (s, 9H), 1.0 (d, 3H), 0.8 (d, 3H) ppm.

Step (d) Preparation of (R) 3-Methyl-2-(6,7,8 9-tetrahydro-dibenzofuran-3-sulfonylamino)-butyric acid To a solution of anisole (0.062 g, 0.57 mmol) in trifluoroacetic acid (3 mL) stirred at room temperature was added (R) 3-methyl-2-(6,7,8,9-tetrahydro-dibenzofuran-3-sulfonylamino)-butyric acid, tert-butyl ester (0.23 g, 0.56 mmol). Hydrolysis of the ester was completed in 4 hours, at which time the acidic solution was poured over ice, and the resulting solid was collected by filtration. The filter cake was dried in vacuo, and the solid was recrystallized from hexane/ethyl acetate to yield a cream-colored powder (0.12 g, 71%); mp 167–169° C. $^1$HNMR (CDCl$_3$) δ7.9 (s, 1H), 7.7 (d, 1H), 7.4 (d, 1H), 5.4 (d, 1H), 3.7 (dd, 1H), 2.7 (m, 2H), 2.5 (m, 2H), 2.1 (m, 1H), 1.9–1.7 (m, 4H), 0.9 (d, 3H), 0.8 (d, 3H) ppm.

In a manner similar to that described in Example 1, the following compounds were prepared:

EXAMPLE 2

(S) 3-Methyl-2-(6,7,8,9-tetrahydro-dibenzofuran-3-sulfonylamino)-butyric acid mp 162–165° C.

$^1$HNMR (CDCl$_3$) δ7.9 (s, 1H), 7.7 (d, 1H), 7.5 (d, 1H), 5.1 (d, 1H), 3.8 (dd, 1H), 2.8 (m, 2H), 2.6 (m, 2H), 2.1 (m, 1H), 2.0–1.8 (m, 4H), 0.9 (d, 3H), 0.8 (d, 3H) ppm.

EXAMPLE 3

(S) 2-(6,7,8,9-Tetrahydro-dibenzofuran-3-sulfonylamino)-succinic acid mp 176–179° C.

$^1$HNMR (CDCl$_3$/DMSO-d$_6$) δ7.8 (s, 1H), 7.6 (d, 1H), 7.4 (d, 1H), 5.9 (d, 1H), 3.9 (m, 1H), 2.9–2.5 (m, 7H), 1.9–1.7 (m, 4H) ppm.

In a manner similar to that described in Example 1 but replacing D-valine, tert-butyl ester with L-homophenylalanine, methyl ester and utilizing basic hydrolysis of the ester moiety, the following compound was prepared:

EXAMPLE 4

(S) 4-Phenyl-2-(6,7,8,9-tetrahydro-dibenzofuran-3-sulfonylamino)-butyric acid mp 167–169° C.

$^1$HNMR (CDCl$_3$) δ7.9 (s, 1H), 7.7 (d, 1H), 7.5 (d, 1H), 7.2 (m, 3H), 7.1 (d, 2H), 5.2 (d, 1H), 4.0 (m, 1H).

Using the procedure of Example 1, the following compounds of Formula I are prepared:

EXAMPLE 5

(S)-Phenyl-[(6,7,8,9-tetrahydro-dibenzofuran-3-sulfonylamino)]-acetic acid

EXAMPLE 6

(S) 5-Phenyl-2-(6,7,8,9-tetrahydro-dibenzofuran-3-sulfonylamino)-pentanoic acid

EXAMPLE 7

2-(2,3-Dihydro-1H-8-oxa-cyclpenta[a]indene-6-sulfonylamino)3-methyl-butyric acid

EXAMPLE 8

(S) 3-Methyl-2-(6,7,8,9-tetrahydro-5H-10-oxa-benzo[a]azulene-2-sulfonylamino)-butyric acid

EXAMPLE 9

(S) N-Hydroxy-4-phenyl-2-(6,7,8,9-tetrahydro-dibenzofuran-3-sulfonylamino)-butyramide

EXAMPLE 10

(S) N-Hydroxy-3-(6,7,8,9-tetrahydro-dibenzofuran-3-sulfonylamino)-succinamic acid

EXAMPLE 11

(R) 4-Phenyl-2-(6,7,8,9-tetrahydro-dibenzofuran-3-sulfonylamino)-butyric acid

EXAMPLE 12

(R) 2-(6,7,8,9-Tetrahydro-dibenzofuran-3-sulfonylamino)-succinic acid

EXAMPLE 13

(R) 2-(2,3-Dihydro-1H-8-oxa-cyclopenta[a]indene-6-sulfonylamino)-3-methyl-butyric acid

EXAMPLE 14

(R) 3-Methyl-2-(6,7,8,9-tetrahydro-5H-10-oxa-benzo[a]azulene-2-sulfonylamino)-butyric acid

EXAMPLE 15

(S) 3-Methyl-2-(6,7,8,9-tetrahydro-dibenzothiophene-3-sulfonylamino)-butyric acid

EXAMPLE 16

(S) 3-Methyl-2-(9-methyl-6,7,8,9-tetrahydro-5H-carbazole-2-sulfonylamino)-butyric acid

EXAMPLE 17

(S) 4-Phenyl-2-(6,7,8,9-tetrahydro-5H-fluorene-2-sulfonylamino)-butyric acid

EXAMPLE 18

(S) 3-Methyl-2-(6,7,8,9-tetrahydro-5H-fluorene-2-sulfonylamino)-butyric acid

GENERAL PROCEDURE FOR PREPARING HYDROXAMIC ACIDS OF FORMULA I (Y=NHOH)

Step (a) Preparation of O-Benzylhydroxylamine Derivative

To a solution of the acid chloride of a carboxylic acid of Formula I (Y=OH) in tetrahydrofuran is added two equivalents of O-benzylhydroxylamine (the acid chloride is prepared from the corresponding acid and thionyl chloride or oxalyl chloride). The mixture is stirred at room temperature for 24 hours. The reaction mixture is diluted with 1 M hydrochloric acid and ethyl acetate. The layers are separated and the ethyl acetate solution is washed with water and dried over magnesium sulfate. After filtration, the crude solid is triturated with hexane, and the resulting solid is collected by filtration.

Step (b) Preparation of Hydroxamic Acid of Formula I (Y=NHOH)

To a solution of the product from Step (a) in methanol/tetrahydrofuran is added palladium on barium sulfate. The solution is exposed to hydrogen gas either at atmospheric pressure under a balloon or at 50 pounds per square inch (psi) in a Parr apparatus. After hydrogen uptake is complete, the mixture is filtered through celite and concentrated in vacuo to afford the hydroxamic acid.

Using the general procedure for preparing hydroxamic acids described above, the following hydroxamic acids of Formula I are prepared.

EXAMPLE 19
(S) N-Hydroxy-3-methyl-2-(6,7,8,9-tetrahydro-dibenzofuran-3-sulfonylamino)-butyramide

EXAMPLE 20
(S) N-Hydroxy-4-phenyl-2-(6,7,8,9-tetrahydro-dibenzofuran-3-sulfonylamino)-butyramide

EXAMPLE 21
(S) N-Hydroxy-2-phenyl-2-(6,7,8,9-tetrahydro-dibenzofuran-3-sulfonylamino)-acetamide

EXAMPLE 22
(S) N-Hydroxy-2-(6,7,8,9-tetrahydro-dibenzofuran-3-sulfonylamino)-3-(3,4,4-trimethyl-2,5-dioxo-imidazolidin-1-yl)-propionamide

EXAMPLE 23
(S) 3-(1,3-Dioxo-1,3-dihydro-isoindol-2-yl)-N-hydroxy-2-(6,7,8,9-tetrahydro-dibenzofuran-3-sulfonylamino)-propionamide

EXAMPLE 24
(S) 5-Phenyl-2-(6,7,8,9-tetrahydro-dibenzofuran-3-sulfonylamino)-pentanoic acid hydroxyamide

EXAMPLE 25
(S) N-Hydroxy-3-(1H-indol-3-yl)-2-(6,7,8,9-tetrahydro-dibenzofuran-3-sulfonylamino)-propionamide

EXAMPLE 26
(S) 2-(2,3-Dihydro-1H-8-oxa-cyclopenta[a]indene-6-sulfonylamino)-N-hydroxy-3-methyl-butyramide

EXAMPLE 27
(S) N-Hydroxy-3-methyl-2-(6,7,8,9-tetrahydro-5H-10-oxa-benzo[a]azulene-2-sulfonylamino)-butyramide

EXAMPLE 28
(S) N-Hydroxy-4-phenyl-2-(6,7,8,9-tetrahydro-5H-fluorene-2-sulfonylamino)-butyramide

EXAMPLE 29
(S) N-Hydroxy-3-methyl-2-(6,7,8,9-tetrahydro-5H-fluorene-2-sulfonylamino)-butyramide

EXAMPLE 30
(R) N-Hydroxy-3-methyl-2-(6,7,8,9-tetrahydro-dibenzofuran-3-sulfonylamino)-butyramide

EXAMPLE 31
(R) N-Hydroxy-4-phenyl-2-(6,7,8,9-tetrahydro-dibenzofuran-3-sulfonylamino)-butyramide

EXAMPLE 32
(R) N-Hydroxy-2-phenyl-2-(6,7,8,9-tetrahydro-dibenzofuran-3-sulfonylamino)-acetamide

EXAMPLE 33
(R) N-Hydroxy-2-(6,7,8,9-tetrahydro-dibenzofuran-3-sulfonylamino)-3-(3,4,4-trimethyl-2,5-dioxo-imidazolidin-1-yl)-propionamide

EXAMPLE 34
(R) 3-(1,3-Dioxo-1,3-dihydro-isoindol-2-yl)-N-hydroxy-2-(6,7,8,9-tetrahydro-dibenzofuran-3-sulfonylamino)-propionamide

EXAMPLE 35
(R) 5-Phenyl-2-(6,7,8,9-tetrahydro-dibenzofuran-3-sulfonylamino)-pentanoic acid hydroxyamide

EXAMPLE 36
(R) N-Hydroxy-3-(1H-indol-3-yl)-2-(6,7,8,9-tetrahydro-dibenzofuran-3-sulfonylamino)-propionamide

EXAMPLE 37
(R) 2-(2,3-Dihydro-1H-8-oxa-cyclopenta[a]indene-6-sulfonylamino)-N-hydroxy-3-methyl-butyramide

EXAMPLE 38
(R) N Hydroxy-3-methyl-2-(6,7,8,9-tetrahydro-5H-10-oxa-benzo[a]azulene-2-sulfonylamino)-butyramide

EXAMPLE 39
(R) N-Hydroxy-4-phenyl-2-(6,7,8,9-tetrahydro-5H-fluorene-2-sulfonylamino)-butyramide

EXAMPLE 40
(R) N-Hydroxy-3-methyl-2-(6,7,8,9-tetrahydro-5H-fluorene-2-sulfonylamino)-butyramide

What is claimed is:

1. A compound of Formula I

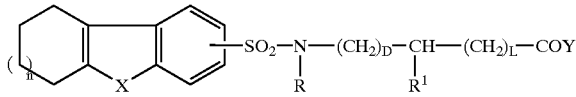

wherein n is zero or an integer of 1 or 2;

X is —O—;

R is hydrogen,
   alkyl,
   hydroxyalkyl,
   alkoxyalkyl,
   trifluoromethyl,
   alkanoyloxyalkyl,
   alkanoylaminoalkyl,
   alkylthioalkyl,
   alkylsulfinylalkyl,
   alkylsulfonylalkyl,
   aminoalkyl,
   alkylaminoalkyl,
   dialkylaminoalkyl,
   N-alkylpiperazinoalkyl,
   N-phenylalkylpiperazinoalkyl,
   morpholinoalkyl,
   thiomorpholinoalkyl,
   piperidinoalkyl,
   pyrrolidinoalkyl, N-alkylalkylpiperidinoalkyl,
pyridylalkyl,
thienylalkyl,
quinolinylalkyl,
thiazolylalkyl,
cycloalkyl,
cycloalkylalkyl,
phenyl,
phenyl substituted by one to three substituents selected from the group consisting of:
  hydroxy,
  alkoxy,
  alkyl,
  alkylthio,
  alkylsulfinyl,
  alkylsulfonyl,
  amino,
  alkylamino,
  dialkylamino,
  halogen,
  cyano,
  nitro,
  trifluoromethyl or on adjacent carbon atoms by either a one to two carbon alkenylenedioxy group or a two to three carbon alkenyleneoxy group,
phenylalkyl,
phenylalkyl wherein phenyl is substituted by alkyl,
  alkoxy,
  halogen, or
  trifluoromethyl,
heteroaryl,
heteroaryl substituted by one to two substituents selected from the group consisting of:
  alkyl, or
  halogen,
biphenyl,
biphenyl, substituted by alkyl,
  alkoxy,
  halogen,
  trifluoromethyl, or
  cyano,
biphenylalkyl or
biphenylalkyl wherein biphenyl is substituted by
  alkyl,
  alkoxy,
  halogen,
  trifluoromethyl, or
  cyano;
D is zero or an integer of 1 to 3;
L is zero or an integer of 1 to 3;
$R^1$ is hydrogen
  a side chain or a natural amino acid or
  a side chain of an unnatural amino acid;
Y is $OR^3$ wherein $R^3$ is hydrogen,
  methyl,
  ethyl, or
  benzyl, or
NH—$OR^4$ wherein $R^4$ is hydrogen,
  alkyl, or
  benzyl;
and corresponding isomers thereof; or a pharmaceutically acceptable salt thereof.

2. The compound according to claim 1 which is

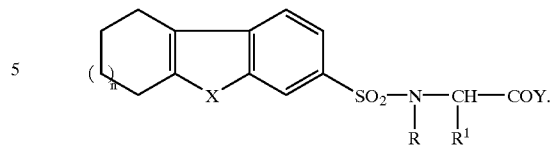

3. The compound according to claim 2 wherein
n is zero or an integer of 1; and
X is —O—.
4. The compound according to claim 3 wherein
n is zero or an integer of 1;
X is —O—; and
R is hydrogen.
5. The compound according to claim 4 wherein
n is zero or an integer of 1;
X is —O—;
R is hydrogen; and
Y is OH.
6. The compound according to claim 1 wherein
n is zero or an integer of 1;
X is —O—;
R is hydrogen; and
Y is NHOH.
7. A compound selected from the group consisting of:
(S) 3-Methyl-2-(6,7,8,9-tetrahydro-dibenzofuran-3-sulfonylamino)-butyric acid;
(S) N-Hydroxy-3-methyl-2-(6,7,8,9-tetrahydro-dibenzofuran-3-sulfonylamino)-butyramide;
(S) 4-Phenyl-2-(6,7,8,9-tetrahydro-dibenzofuran-3-sulfonylamino)-butyric acid;
(S) 2-(6,7,8,9-Tetrahydro-dibenzofuran-3-sulfonylamino)-succinic acid;
(S) Phenyl-[(6,7,8,9-tetrahydro-dibenzofuran-3-sulfonylamino)]-acetic acid;
(S) 2-(6,7,8,9-Tetrahydro-dibenzofuran-3-sulfonylamino)-3-(3,4,4-trimethyl-2,5-dioxo-imidazolidin-1-yl)-propionic acid;
(S) 3-(1,3-Dioxo-1,3-dihydro-isoindol-2-yl)-2-(6,7,8,9-tetrahydro-dibenzofuran-3-sulfonylamino)-propionic acid;
(S) 2-(6,7,8,9-Tetrahydro-dibenzofuran-3-sulfonylamino)-4-(3,4,4-trimethyl-2,5-dioxo-imidazolidin-1-yl)-butyric acid;
(S) 2-(6,7,8,9-Tetrahydro-dibenzofuran-3-sulfonylamino)-5-(3,4,4-trimethyl-2,5-dioxo-imidazolidin-1-yl)-pentanoic acid;
(S) 5-Phenyl-2-(6,7,8,9-tetrahydro-dibenzofuran-3-sulfonylamino)-pentanoic acid;
(S) 4-Phenylmethanesulfinyl-2-(6,7,8,9-tetrahydro-dibenzofuran-3-sulfonylamino)-butyric acid;
(S) 4-(1,3-Dioxo-1,3-dihydro-isoindol-2-yl)-2-(6,7,8,9-tetrahydro-dibenzofuran-3-sulfonylamino)-butyric acid;
(S) 5-(1,3-Dioxo-1,3-dihydro-isoindol-2-yl)-2-(6,7,8,9-tetrahydro-dibenzofuran-3-sulfonylamino)-pentanoic acid;
(S) 6-Phenyl-2-(6,7,8,9-tetrahydro-dibenzofuran-3-sulfonylamino)-hexanoic acid;
(S) 7-Phenyl-2-(6,7,8,9-tetrahydro-dibenzofuran-3-sulfonylamino)-heptanoic acid;
(S) 8-Phenyl-2-(6,7,8,9-tetrahydro-dibenzofuran-3-sulfonylamino)-octanoic acid;
(S) 4-Phenylsulfamoyl-2-(6,7,8,9-tetrahydro-dibenzofuran-3-sulfonylamino)-butyric acid;

(S) 4-Phenylmethanesulfonyl-2-(6,7,8,9-tetrahydro-dibenzofuran-3-sulfonylamino)-butyric acid;
(S) 4-Benzylsulfanyl-2-(6,7,8,9-tetrahydro-dibenzofuran-3-sulfonylamino)-butyric acid;
(S) 3-(1H-Indol-3-yl)-2-(6,7,8,9-tetrahydro-dibenzofuran-3-sulfonylamino)-propionic acid;
(S) 4-(1H-Indol-3-yl)-2-(6,7,8,9-tetrahydro-dibenzofuran-3-sulfonylamino)-butyric acid;
(S) 5-(1H-Indol-3-yl)-2-(6,7,8,9-tetrahydro-dibenzofuran-3-sulfonylamino)-pentanoic acid;
(S) 6-(1H-Indol-3-yl)-2-(6,7,8,9-tetrahydro-dibenzofuran-3-sulfonylamino)-hexanoic acid;
(S) 7-(1H-Indol-3-yl)-2-(6,7,8,9-tetrahydro-dibenzofuran-3-sulfonylamino)-heptanoic acid;
(S) 8-(1H-Indol-3-yl)-2-(6,7,8,9-tetrahydro-dibenzofuran-3-sulfonylamino)-octanoic acid;
(S) N-Hydroxy-4-phenyl-2-(6,7,8,9-tetrahydro-dibenzofuran-3-sulfonylamino)-butyramide;
(S) N-Hydroxy-3-(6,7,8,9-tetrahydro-dibenzofuran-3-sulfonylamino)-succinamic acid;
(S) N-Hydroxy-2-phenyl-2-(6,7,8,9-tetrahydro-dibenzofuran-3-sulfonylamino)-acetamide
(S) N-Hydroxy-2-(6,7,8,9-tetrahydro-dibenzofuran-3-sulfonylamino)-3-(3,4,4-trimethyl-2,5-dioxo-imidazolidin-1-yl)-propionamide;
(S) 3-(1,3-Dioxo-1,3-dihydro-isoindol-2-yl)-N-hydroxy-2-(6,7,8,9-tetrahydro-dibenzofuran-3-sulfonylamino)-propionamide;
(S) N-Hydroxy-2-(6,7,8,9-tetrahydro-dibenzofuran-3-sulfonylamino)-4-(3,4,4-trimethyl-2,5-dioxo-imidazolidin-1-yl)-butyramide;
(S) 2-(6,7,8,9-Tetrahydro-dibenzofuran-3-sulfonylamino)-5-(3,4,4-trimethyl-2,5-dioxo-imidazolidin-1-yl)-pentanoic acid hydroxyamide;
(S) 5-Phenyl-2-(6,7,8,9-tetrahydro-dibenzofuran-3-sulfonylamino)-pentanoic acid hydroxyamide;
(S) N-Hydroxy-4-phenylmethanesulfinyl-2-(6,7,8,9-tetrahydro-dibenzofuran-3-sulfonylamino)-butyramide;
(s) 4-(1,3-Dioxo-1,3-dihydro-isoindol-2-yl)-N-hydroxy-2-(6,7,8,9-tetrahydro-dibenzofuran-3-sulfonylamino)-butyramide;
(S) 5-(1,3-Dioxo-1,3-dihydro-isoindol-2-yl)-2-(6,7,8,9-tetrahydro-dibenzofuran-3-sulfonylamino)-pentanoic acid hydroxyamide;
(S) 6-Phenyl-2-(6,7,8,9-tetrahydro-dibenzofuran-3-sulfonylamino)-hexanoic acid hydroxyamide;
(S) 7-Phenyl-2-(6,7,8,9-tetrahydro-dibenzofuran-3-sulfonylamino)-heptanoic acid hydroxyamide;
(S) 8-Phenyl-2-(6,7,8,9-tetrahydro-dibenzofuran-3-sulfonylamino)-octanoic acid hydroxyamide;
(S) 4-Benzylsulfanyl-N-hydroxy-2-(6,7,8,9-tetrahydro-dibenzofuran-3-sulfonylamino)-butyramide;
(S) N-Hydroxy-4-phenylsulfamoyl-2-(6,7,8,9-tetrahydro-dibenzofuran-3-sulfonylamino)-butyramide;
(S) N-Hydroxy-4-phenylmethanesulfonyl-2-(6,7,8,9-tetrahydro-dibenzofuran-3-sulfonylamino)-butyramide;
(S) N-Hydroxy-3-(1H-indol-3-yl)-2-(6,7,8,9-tetrahydro-dibenzofuran-3-sulfonylamino)-propionamide;
(S) N-Hydroxy-4-(1H-indol-3-yl)-2-(6,7,8,9-tetrahydro-dibenzofuran-3-sulfonylamino)-butyramide;
(S) 5-(1H-Indol-3-yl)-2-(6,7,8,9-tetrahydro-dibenzofuran-3-sulfonylamino)-pentanoic acid hydroxyamide;
(S) 6-(1H-Indol-3-yl)-2-(6,7,8,9-tetrahydro-dibenzofuran-3-sulfonylamino)-hexanoic acid hydroxyamide;
(S) 7-(1H-Indol-3-yl)-2-(6,7,8,9-tetrahydro-dibenzofuran-3-sulfonylamino)-heptanoic acid hydroxyamide;
(S) 8-(1H-Indol-3-yl)-2-(6,7,8,9-tetrahydro-dibenzofuran-3-sulfonylamino)-octanoic acid hydroxyamide;
(R) 3-Methyl-2-(6,7,8,9-tetrahydro-dibenzofuran-3-sulfonylamino)-butyric acid;
(R) N-Hydroxy-3-methyl-2-(6,7,8,9-tetrahydro-dibenzofuran-3-sulfonylamino)-butyramide;
(R) 4-Phenyl-2-(6,7,8,9-tetrahydro-dibenzofuran-3-sulfonylamino)-butyric acid;
(R) 2-(6,7,8,9-Tetrahydro-dibenzofuran-3-sulfonylamino)-succinic acid;
(R) Phenyl-[(6,7,8,9-tetrahydro-dibenzofuran-3-sulfonylamino)]-acetic acid;
(R) 2-(6,7,8,9-Tetrahydro-dibenzofuran-3-sulfonylamino)-3-(3,4,4-trimethyl-2,5-dioxo-imidazolidin-1-yl)-propionic acid;
(R) 3-(1,3-Dioxo-1,3-dihydro-isoindol-2-yl)-2-(6,7,8,9-tetrahydro-dibenzofuran-3-sulfonylamino)-propionic acid;
(R) 2-(6,7,8,9-Tetrahydro-dibenzofuran-3-sulfonylamino)-4-(3,4,4-trimethyl-2,5-dioxo-imidazolidin-1-yl)-butyric acid;
(R) 2-(6,7,8,9-Tetrahydro-dibenzofuran-3-sulfonylamino)-5-(3,4,4-trimethyl-2,5-dioxo-imidazolidin-1-yl)-pentanoic acid;
(R) 5-Phenyl-2-(6,7,8,9-tetrahydro-dibenzofuran-3-sulfonylamino)-pentanoic acid;
(R) 4-Phenylmethanesulfinyl-2-(6,7,8,9-tetrahydro-dibenzofuran-3-sulfonylamino)-butyric acid;
(R) 4-(1,3-Dioxo-1,3-dihydro-isoindol-2-yl)-2-(6,7,8,9-tetrahydro-dibenzofuran-3-sulfonylamino)-butyric acid;
(R) 5-(1,3-Dioxo-1,3-dihydro-isoindol-2-yl)-2-(6,7,8,9-tetrahydro-dibenzofuran-3-sulfonylamino)-pentanoic acid;
(R) 6-Phenyl-2-(6,7,8,9-tetrahydro-dibenzofuran-3-sulfonylamino)-hexanoic acid;
(R) 7-Phenyl-2-(6,7,8,9-tetrahydro-dibenzofuran-3-sulfonylamino)-heptanoic acid;
(R) 8-Phenyl-2-(6,7,8,9-tetrahydro-dibenzofuran-3-sulfonylamino)-octanoic acid;
(R) 4-Phenylsulfamoyl-2-(6,7,8,9-tetrahydro-dibenzofuran-3-sulfonylamino)-butyric acid;
(R) 4-Phenylmethanesulfonyl-2-(6,7,8,9-tetrahydro-dibenzofuran-3-sulfonylamino)-butyric acid;
(R) 4-Benzylsulfanyl-2-(6,7,8,9-tetrahydro-dibenzofuran-3-sulfonylamino)-butyric acid;
(R) 3-(1H-Indol-3-yl)-2-(6,7,8,9-tetrahydro-dibenzofuran-3-sulfonylamino)-propionic acid;
(R) 4-(1H-Indol-3-yl)-2-(6,7,8,9-tetrahydro-dibenzofuran-3-sulfonylamino)-butyric acid;
(R) 5-(1H-Indol-3-yl)-2-(6,7,8,9-tetrahydro-dibenzofuran-3-sulfonylamino)-pentanoic acid;
(R) 6-(1H-Indol-3-yl)-2-(6,7,8,9-tetrahydro-dibenzofuran-3-sulfonylamino)-hexanoic acid;
(R) 7-(1H-Indol-3-yl)-2-(6,7,8,9-tetrahydro-dibenzofuran-3-sulfonylamino)-heptanoic acid;
(R) 8-(1H-Indol-3-yl)-2-(6,7,8,9-tetrahydro-dibenzofuran-3-sulfonylamino)-octanoic acid;
(R) N-Hydroxy-4-phenyl-2-(6,7,8,9-tetrahydro-dibenzofuran-3-sulfonylamino)-butyramide;
(R) N-Hydroxy-3-(6,7,8,9-tetrahydro-dibenzofuran-3-sulfonylamino)-succinamic acid;
(R) N-Hydroxy-2-phenyl-2-(6,7,8,9-tetrahydro-dibenzofuran-3-sulfonylamino)-acetamide;
(R) N-Hydroxy-2-(6,7,8,9-tetrahydro-dibenzofuran-3-sulfonylamino)-3-(3,4,4-trimethyl-2,5-dioxo-imidazolidin-1-yl)-propionamide;
(R) 3-(1,3-Dioxo-1,3-dihydro-isoindol-2-yl)-N-hydroxy-2-(6,7,8,9-tetrahydro-dibenzofuran-3-sulfonylamino)-propionamide;

(R) N-Hydroxy-2-(6,7,8,9-tetrahydro-dibenzofuran-3-sulfonylamino)-4-(3,4,4-trimethyl-2,5-dioxo-imidazolidin-1-yl)-butyramide;
(R) 2-(6,7,8,9-Tetrahydro-dibenzofuran-3-sulfonylamino)-5-(3,4,4-trimethyl-2,5-dioxo-imidazolidin-1-yl)-pentanoic acid hydroxyamide;
(R) 5-Phenyl-2-(6,7,8,9-tetrahydro-dibenzofuran-3-sulfonylamino)-pentanoic acid hydroxyamide;
(R) N-Hydroxy-4-phenylmethanesulfinyl-2-(6,7,8,9-tetrahydro-dibenzofuran-3-sulfonylamino)-butyramide
(R) 4-(1,3-Dioxo-1,3-dihydro-isoindol-2-yl)-N-hydroxy-2-(6,7,8,9-tetrahydro-dibenzofuran-3-sulfonylamino)-butyramide;
(R) 5-(1,3-Dioxo-1,3-dihydro-isoindol-2-yl)-2-(6,7,8,9-tetrahydro-dibenzofuran-3-sulfonylamino)-pentanoic acid hydroxyamide;
(R) 6-Phenyl-2-(6,7,8,9-tetrahydro-dibenzofuran-3-sulfonylamino)-hexanoic acid hydroxyamide;
(R) 7-Phenyl-2-(6,7,8,9-tetrahydro-dibenzofuran-3-sulfonylamino)-heptanoic acid hydroxyamide;
(R) 8-Phenyl-2-(6,7,8,9-tetrahydro-dibenzofuran-3-sulfonylamino)-octanoic acid hydroxyamide;
(R) 4-Benzylsulfanyl-N-hydroxy-2-(6,7,8,9-tetrahydro-dibenzofuran-3-sulfonylamino)-butyramide;
(R) N-Hydroxy-4-phenylsulfamoyl-2-(6,7,8,9-tetrahydro-dibenzofuran-3-sulfonylamino)-butyramide;
(R) N-Hydroxy-4-phenylmethanesulfonyl-2-(6,7,8,9-tetrahydro-dibenzofuran-3-sulfonylamino)-butyramide;
(R) N-Hydroxy-3-(1H-indol-$^3$-yl)-2-(6,7,8,9-tetrahydro-dibenzofuran-3-sulfonylamino)-propionamide;
(R) N-Hydroxy-4-(1H-indol-3-yl)-2-(6,7,8,9-tetrahydro-dibenzofuran-3-sulfonylamino)-butyramide;
(R) 5-(1H-Indol-3-yl)-2-6,7,8,9-tetrahydro-dibenzofuran-3-sulfonylamino)-pentanoic acid hydroxyamide;
(R) 6-(1H-Indol-3-yl)-2-(6,7,8,9-tetrahydro-dibenzofuran-3-sulfonylamino)-hexanoic acid hydroxyamide;
(R) 7-(1H-Indol-3-yl)-2-(6,7,8,9-tetrahydro-dibenzofuran-3-sulfonylamino)-heptanoic acid hydroxyamide;
(R) 8-(1H-Indol-3-yl)-2-(6,7,8,9-tetrahydro-dibenzofuran-3-sulfonylamino)-octanoic acid hydroxyamide;
and corresponding isomers thereof; or a pharmaceutically acceptable salt thereof.

8. A method of inhibiting a matrix metalloproteinase comprising administering to a host suffering therefrom a therapeutically effective amount of a compound according to claim 1 in unit dosage form.

9. A method of inhibiting gelatinase A comprising administering to a host suffering therefrom a therapeutically effective amount of a compound according to claim 1 in unit dosage form.

10. A method of inhibiting stromelysin-1 comprising administering to a host suffering therefrom a therapeutically effective amount of a compound according to claim 1 in unit dosage form.

11. A method of inhibiting collagenase-3 comprising administering to a host suffering therefrom a therapeutically effective amount of a compound according to claim 1 in unit dosage form.

12. A method of preventing atherosclerotic plaque rupture comprising administering to a host suffering therefrom a therapeutically effective amount of a compound according to claim 1 in unit dosage form.

13. A method of inhibiting aortic aneurysm comprising administering to a host suffering therefrom a therapeutically effective amount of a compound according to claim 1 in unit dosage form.

14. A method of inhibiting heart failure comprising administering to a host suffering therefrom a therapeutically effective amount of a compound according to claim 1 in unit dosage form.

15. A method of preventing restenosis comprising administering to a host suffer therefrom a therapeutically effective amount of a compound according to claim 1 in unit dosage form.

16. A method of controlling periodontal disease comprising administering to a host suffering therefrom a therapeutically effective amount of a compound according to claim 1 in unit dosage form.

17. A method of treating corneal ulceration comprising administering to a host suffering therefrom a therapeutically effective amount of a compound according to claim 1 in unit dosage form.

18. A method of treating burns comprising administering to a host suffering therefrom a therapeutically effective amount of a compound according to claim 1 in unit dosage form.

19. A method of treating decubital ulcers comprising administering to a host suffering therefrom a therapeutically effective amount of a compound according to claim 1 in unit dosage form.

20. A method of treatment for healing wounds comprising administering to a host suffering therefrom a therapeutically effective amount of a compound according to claim 1 in unit dosage form.

21. A method of treating cancer comprising administering to a host suffering therefrom a therapeutically effective amount of a compound according to claim 1 in unit dosage form.

22. A method of treating arthritis comprising administering to a host suffering therefrom a therapeutically effective amount of a compound according to claim 1 in unit dosage form.

23. A method of treating osteoporosis comprising administering to a host suffering therefrom a therapeutically effective amount of a compound according to claim 1 in unit dosage form.

24. A method of treating autoimmune or inflammatory disorders dependent upon tissue invasion by leukocytes comprising administering to a host suffering therefrom a therapeutically effective amount of a compound according to claim 1 in unit dosage form.

25. A method of treating multiple sclerosis comprising administering to a host suffering therefrom a therapeutically effective amount of a compound according to claim 1 in unit dosage form.

26. A method of treating inflammation and pain comprising administering to a host suffering therefrom a therapeutically effective amount of a compound according to claim 1 in unit dosage form.

27. A method of treating acute and chronic neurodegenerative disorders selected from the group consisting of: stroke, head trauma, spinal cord injury, Alzheimer's disease, amyotrophic lateral sclerosis, cerebral amyloid angiopathy, AIDS, Parkinson's disease, Huntington's diseases, prion diseases, myasthenia gravis, and Duchenne's muscular dystrophy comprising administering to a host suffering therefrom a therapeutically effective amount of a compound according to claim 1 in unit dosage form.

28. A method of treating renal disease comprising administering to a host suffering therefrom a therapeutically effective amount of a compound according to claim 1 in unit dosage form.

29. A method of treating left ventricular dilation comprising administering to a host suffering therefrom a therapeutically effective amount of a compound according to claim 1 in unit dosage form.

30. A pharmaceutical composition comprising a compound according to claim 1 in admixture with a pharmaceutically acceptable excipient, diluent, or carrier.

31. A method for preparing a compound of Formula Ie

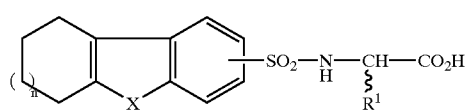

wherein n is zero or an integer of 1 or 2;

X is —O—; and $R^1$ is hydrogen, a side chain of a natural amino acid or a side chain of an unnatural amino acid; and corresponding isomers thereof; or a pharmaceutically acceptable salt thereof which comprises a compound of formula (15)

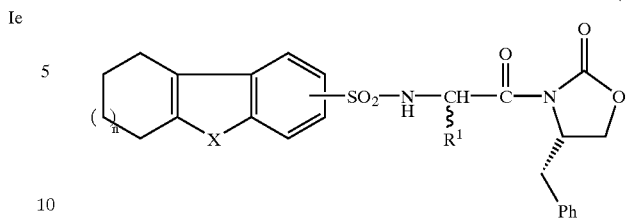

wherein Ph is phenyl and n, X, and $R^1$ are as defined above with a base in a solvent to give a compound of Formula Ie and if desired, converting a compound of compound of Formula Ie to a corresponding pharmaceutically acceptable salt by conventional means and, if so desired, converting the corresponding pharmaceutically acceptable salt to a compound of Formula Ie by conventional means.

* * * * *

UNITED STATES PATENT AND TRADEMARK OFFICE
CERTIFICATE OF CORRECTION

PATENT NO. : 6,420,408 B1
DATED : July 16, 2002
INVENTOR(S) : O'Brien et al.

It is certified that error appears in the above-identified patent and that said Letters Patent is hereby corrected as shown below:

<u>Title page,</u>
Insert the following:
-- [22]  PCT Filed:          June 2, 1999
   [86]  PCT No.:            PCT/US99/12273
         § 371 Date:          April 10, 2001
         § 102(e) Date:       April 10, 2001
   [87]  PCT Pub. No.:       WO 00/06561
         PCT Pub. Date:       February 10, 2000 --

Item [56], References Cited, OTHER PUBLICATIONS, 14th reference, "Internatioal" should read -- International --

<u>Column 43,</u>
Line 28, "(1H-indol-$^3$-yl)" should read -- (1H-indol-3-yl) --
Line 32, "2-6,7,8,9" should read -- 2-(6,7,8,9 --

<u>Column 46,</u>
Line 15, delete second "compound of"

Signed and Sealed this

Fourth Day of February, 2003

JAMES E. ROGAN
*Director of the United States Patent and Trademark Office*